United States Patent
Wilson

(10) Patent No.: US 12,297,502 B2
(45) Date of Patent: *May 13, 2025

(54) METHODS AND COMPOSITIONS FOR DETECTING AND DIAGNOSING DISEASES AND CONDITIONS

(71) Applicant: Stealth BioTherapeutics Inc., Needham, MA (US)

(72) Inventor: D. Travis Wilson, Newton, MA (US)

(73) Assignee: STEALTH BIOTHERAPEUTICS INC., Needham, MA (US)

( * ) Notice: Subject to any disclaimer, the term of this patent is extended or adjusted under 35 U.S.C. 154(b) by 182 days.

This patent is subject to a terminal disclaimer.

(21) Appl. No.: 17/708,909

(22) Filed: Mar. 30, 2022

(65) Prior Publication Data

US 2023/0033758 A1 Feb. 2, 2023

Related U.S. Application Data

(60) Continuation of application No. 16/101,078, filed on Aug. 10, 2018, now Pat. No. 11,312,993, which is a division of application No. 14/392,293, filed as application No. PCT/US2014/043711 on Jun. 23, 2014, now Pat. No. 10,047,395.

(60) Provisional application No. 61/840,760, filed on Jun. 28, 2013, provisional application No. 61/839,753, filed on Jun. 26, 2013.

(51) Int. Cl.
| | |
|---|---|
| C12Q 1/68 | (2018.01) |
| C12Q 1/6883 | (2018.01) |
| A61K 38/06 | (2006.01) |
| G01N 33/92 | (2006.01) |

(52) U.S. Cl.
CPC ............ *C12Q 1/6883* (2013.01); *A61K 38/06* (2013.01); *C12Q 2600/106* (2013.01); *C12Q 2600/118* (2013.01); *C12Q 2600/158* (2013.01); *G01N 33/92* (2013.01); *G01N 2405/04* (2013.01); *G01N 2560/00* (2013.01); *G01N 2800/325* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 5,674,534 A | 10/1997 | Zale et al. |
| 5,716,644 A | 2/1998 | Zale et al. |
| 6,468,798 B1 | 10/2002 | Debs et al. |
| 7,550,439 B2 | 6/2009 | Szeto |
| 7,576,061 B2 | 8/2009 | Szeto et al. |
| 7,718,620 B2 | 5/2010 | Szeto et al. |
| 7,781,405 B2 | 8/2010 | Szeto |
| 8,143,219 B2 | 3/2012 | Szeto et al. |
| 8,404,646 B2 | 3/2013 | Schiller et al. |
| 8,592,373 B2 | 11/2013 | Szeto et al. |
| 8,618,061 B2 | 12/2013 | Szeto |
| 8,940,696 B2 | 1/2015 | Szeto et al. |
| 8,957,030 B2 | 2/2015 | Szeto et al. |
| 9,241,933 B2 | 1/2016 | Cohen et al. |
| 9,457,057 B2 | 10/2016 | Tompkins et al. |
| 9,687,519 B2 | 6/2017 | Wilson et al. |
| 10,047,395 B2 | 8/2018 | Wilson |
| 10,793,597 B2 | 10/2020 | Wilson |
| 11,083,771 B2 | 8/2021 | Wilson et al. |
| 11,083,772 B2 | 8/2021 | Wilson et al. |
| 11,312,993 B2 | 4/2022 | Wilson |
| 11,771,734 B2 | 10/2023 | Wilson et al. |
| 2004/0248808 A1 | 12/2004 | Szeto et al. |
| 2006/0084606 A1 | 4/2006 | Szeto |
| 2006/0251641 A1 | 11/2006 | Keimel |
| 2007/0015711 A1 | 1/2007 | Szeto |
| 2007/0026090 A1 | 2/2007 | Tirosh et al. |
| 2007/0027087 A1 | 2/2007 | Szeto et al. |
| 2007/0135335 A1 | 6/2007 | Collier et al. |
| 2007/0265216 A1 | 11/2007 | Gross et al. |
| 2008/0318909 A1 | 12/2008 | Sparagna et al. |
| 2009/0143279 A1 | 6/2009 | Mootha et al. |
| 2009/0221514 A1 | 9/2009 | Szeto et al. |
| 2009/0298848 A1 | 12/2009 | Stewart |
| 2009/0305319 A1 | 12/2009 | Baudenbacher et al. |
| 2010/0158995 A1 | 6/2010 | Mill et al. |
| 2010/0190718 A1 | 7/2010 | Schiller et al. |
| 2010/0311664 A1 | 12/2010 | Szeto |
| 2010/0331265 A1 | 12/2010 | Tompkins et al. |

(Continued)

FOREIGN PATENT DOCUMENTS

| | | |
|---|---|---|
| CN | 1787831 A | 6/2006 |
| JP | 2013-521231 | 6/2013 |

(Continued)

OTHER PUBLICATIONS

Notification of Reexamination on CN Patent Application No. 201480022767.2 dated Sep. 1, 2022 (11 pages) (with English Translation).
"The Voice of the Patient: Barth Syndrome" Presentation. Barth Syndrome Foundation, (2019).
Acín-Pérez, et al., "Respiratory Active Mitochondrial Supercomplexes," Molecular Cell,Nov. 21, 2008, vol. 32, No. 4, pp. 529-539.
Aljabri, et al. "Lethal neonatal mitochondrial phenotype caused by a novel polymerase subunit gamma mutation," Medicine, vol. 97, No. 40(e12591) (2018) (pp. 1-7).
Amselem, et al., "A Large-Scale Method for the Preparation of Sterile and Nonpyrogenic Liposomal Formulations of Defined Size Distributions for Clinical Use." Liposome Technology, 1993, vol. I, 2nd ed., CRC Press, pp. 502-525.

(Continued)

Primary Examiner — Jehanne S Sitton
(74) Attorney, Agent, or Firm — FOLEY & LARDNER LLP

(57) ABSTRACT

The disclosure provides methods for detecting and diagnosing diseases and conditions associated with defects in cardiolipin remodeling. In some embodiments, the present technology relates to methods for detecting the presence or amount of cardiolipin isoforms and/or the presence or amount of enzymes involved in cardiolipin remodeling.

8 Claims, No Drawings

(56) References Cited

U.S. PATENT DOCUMENTS

| | | |
|---|---|---|
| 2011/0008310 A1 | 1/2011 | Cataldo et al. |
| 2011/0039766 A1 | 2/2011 | Szeto |
| 2011/0082084 A1 | 4/2011 | Szeto et al. |
| 2011/0136725 A1 | 6/2011 | Dong |
| 2011/0172312 A1 | 7/2011 | Miller et al. |
| 2011/0177047 A1 | 7/2011 | Liu et al. |
| 2011/0197294 A1 | 8/2011 | Gottlieb et al. |
| 2012/0021970 A1 | 1/2012 | Schiller et al. |
| 2012/0046363 A1 | 2/2012 | Stanley |
| 2012/0122957 A1 | 5/2012 | Dillin et al. |
| 2013/0017150 A1 | 1/2013 | Szeto et al. |
| 2013/0040901 A1 | 2/2013 | Szeto et al. |
| 2013/0244957 A1 | 9/2013 | Szeto et al. |
| 2013/0288985 A1 | 10/2013 | Jurkunas |
| 2013/0345312 A1 | 12/2013 | Jankowski et al. |
| 2014/0031432 A1 | 1/2014 | Jankowski et al. |
| 2014/0107033 A1 | 4/2014 | Szeto et al. |
| 2014/0288012 A1 | 9/2014 | Tompkins et al. |
| 2014/0342004 A1 | 11/2014 | Aprikyan et al. |
| 2014/0349941 A1 | 11/2014 | Wilson et al. |
| 2014/0349942 A1 | 11/2014 | Szeto |
| 2014/0378396 A1 | 12/2014 | Wilson et al. |
| 2015/0010588 A1 | 1/2015 | Szeto |
| 2015/0018288 A1 | 1/2015 | Wilson et al. |
| 2015/0246092 A1 | 9/2015 | Wilson et al. |
| 2015/0266946 A1 | 9/2015 | Sinclair et al. |
| 2015/0353602 A1 | 12/2015 | Szeto et al. |
| 2015/0359838 A1 | 12/2015 | Szeto et al. |
| 2016/0175380 A1 | 6/2016 | Jurkunas |
| 2016/0194708 A1 | 7/2016 | Wilson |
| 2016/0228487 A1 | 8/2016 | Wilson et al. |
| 2016/0361377 A1 | 12/2016 | Wilson et al. |

FOREIGN PATENT DOCUMENTS

| | | |
|---|---|---|
| JP | 6918046 B2 | 8/2021 |
| WO | WO-96/40073 A2 | 12/1996 |
| WO | WO-99/15154 A1 | 4/1999 |
| WO | WO-00/38651 A1 | 7/2000 |
| WO | WO-2004/070054 A2 | 8/2004 |
| WO | WO-2004/070054 A3 | 4/2005 |
| WO | WO-2005/072295 A2 | 8/2005 |
| WO | WO-2006/122140 | 11/2006 |
| WO | WO-2010/120431 A2 | 10/2010 |
| WO | WO-2011/082324 A1 | 7/2011 |
| WO | WO-2011/096398 A1 | 8/2011 |
| WO | WO-2011/106717 A1 | 9/2011 |
| WO | WO-2011/116007 A1 | 9/2011 |
| WO | WO-2011/139992 A1 | 11/2011 |
| WO | WO-2012/129427 | 9/2012 |
| WO | WO-2013/049697 | 4/2013 |
| WO | WO-2014/066419 | 5/2014 |

OTHER PUBLICATIONS

Aprikyan et al. "Advances in the understanding of Barth syndrome," British Journal of Haematology, vol. 161 (2013) (pp. 330-338).
Ashley, et al., "Depletion of mitochondrial DNA in fibroblast cultures from patients with POLG1 mutations is a consequence of catalytic mutations," Hum. Mol. Gene., 2008, vol. 17, No. 16, pp. 2496-2506.
Barth, et al. "An X-linked mitochondrial disease affecting cardiac muscle, skeletal muscle and neutrophil leucocytes," Journal of the Neurological Sciences, vol. 62 (1983) (pp. 327-355).
Birk et al. "The Mitochondrial-Targeted Compound SS-31 Re-Energizes Ischemic Mitochondria by Interacting with Cardiolipin," Journal of the American Society of Nephrology, vol. 24 (2013) (pp. 1250-1261).
Birk, et al., "Targeting cytochrome C for optimization of mitochondrial electron transport chain," FASEB Journal, 2011, vol. 25, No. 1, Abstract.
Blok, et al., "The unfolding clinical spectrum of POLG mutations," J. Med. Genet., 2009, vol. 46, No. 22, pp. 776-785.
CA Office Action on CA Patent Application No. 2916977 dated Mar. 8, 2022 (8 pages).
Calvani et al. "Mitochondrial pathways in sarcopenia of aging and disuse muscle atrophy," Biological Chemistry, vol. 394, No. 3 (2013) (pp. 393-414).
Chinnery, Patrick F. "Mitochondrial Disorders Overview" GeneReviews (2000).
Chonn, et al., "Recent Advances in Liposomal Drug-Delivery Systems," Curr. Opin. Biotechnol., Dec. 1995, vol. 6, Issue 6, pp. 698-708.
Colan, Steven D., "Classification of teh cardiomyopathies," Progress in Pediatric Cardiology, vol. 23, (2007) (pp. 5-15).
Dai et al. "Cardiac Aging: From Molecular Mechanisms to Significance in Human Health and Disease," Antioxidants & Redox Signaling, vol. 16, No. 12 (2012) (pp. 1492-1526).
Dai et al. "Mitochondria and Cardiovascular Aging," Circulation Research, vol. 110 (2012) (pp. 1109-1124).
Dai et al. "Mitochondrial oxidative stress mediates Angiotension II-induced cardiac hypertrophy and Gaq overexpression-induced heart failure," Circulation Research, vol. 108, No. 7 (2011) (pp. 837-846).
Dai, et al., "Mitochondrial targeted antioxidant peptide ameliorates hypertensive cardiomyopathy," Journal of the American College of Cardiology, 2011, vol. 38, No. 1, pp. 73-82.
Decision of Rejection in CN Patent Application No. 201480022764.9 dated Mar. 19, 2019.
Diaz, et al., Cytochrome c Oxidase Is Required for the Assembly/Stability of Respiratory Complex I in Mouse Fibroblasts, Mol. Cell. Bio., Jul. 2006, vol. 26, No. 13, pp. 4872-4881.
Examination Report in EP Patent Application No. 14756991.7 mailed May 11, 2018.
Extended European Search Report on EP Patent Application No. 19190165.1 dated Feb. 5, 2020 (11 pages).
Extended Search Report in EP Patent Application 14757000 No. dated Jul. 16, 2016.
Extended Search Report in EP Patent Application No. 14756991.7 mailed Jul. 19, 2016.
Farina, et al, "MR Findings in Leigh Syndrome with COX deficiency and SURF-1 Mutations," Am. J. Neuroradiol., 2002, vol. 23, pp. 1095-1100.
Ferraris, et al., "Progressive external ophthalmoplegia and vision and hearing loss in a patient with mutations in POLG2 and OPA1," Arch. Neurol., 2008, vol. 65, pp. 125-131.
Final Office Action in U.S. Appl. No. 14/771,411 dated Jan. 25, 2018.
Final Office Action on U.S. Appl. No. 15/626,255 dated Nov. 26, 2018, 13 pages.
Final Office Action on U.S. Appl. No. 16/101,078 dated Sep. 29, 2021 (7 pages).
Final Office Action on U.S. Appl. No. 16/930,028 dated Sep. 17, 2021 (22 pages).
Final Rejection in U.S. Appl. No. 16/929,370 dated Mar. 3, 2021 (7 pages).
Final Rejection on JP Patent Application No. 2019-133638 dated Apr. 4, 2022 (4 pages).
Foreign Action other than Search Report on EP 14757000.6 DTD Sep. 25, 2018.
Foreign Action other than Search Report on JP 2015-560380 DTD Aug. 5, 2019.
Gregoriadis, "Engineering Liposomes for Drug Delivery: Progress and Problems," Trends in Biotechnology, Dec. 1995, vol. 13, No. 12, pp. 527-537.
Han, et al., "Shotgun lipidomics of cardiolipin molecular species in lipid extracts of biological samples," J Lipd Res, 2006, vol. 47, No. 4, pp. 864-879.
He, et al., "Abstract 15771: Mitochondria Targeted Antioxidant Prevents Mitochondrial Dysfunction Induced by Cardiolipin Deficiency," Circulation, Nov. 20, 2012, vol. 126, 2 pages.
Houtkooper, et al., "The Enigmatic Role of Tafazzin in Cardiolipin Metabolism," Biochimica et Biophysica Acta 1788, 2009, pp. 2003-2014.
Houtkooper, et al., "Cardiolipin and monolysocardiolipin analysis in fibroblasts, lymphocytes, and tissues using high-performance

(56) References Cited

OTHER PUBLICATIONS liquid chromatography-mass spectrometry as a diagnostic tests for Barth syndrome," Analytical Biochemistry, 2009, vol. 387, pp. 230-237.
International Search Report and Written Opinion in International Patent Application No. PCT/US14/19622 dated Jun. 3, 2014 (11 pages).
International Search Report and Written Opinion in International Patent Application No. PCT/US14/19645 dated Jun. 17, 2014 (11 pages).
International Search Report and Written Opinion in International Patent Application No. PCT/US14/43711 dated Jan. 2, 2015 (10 pages).
Jefferies, John L. "Barth Syndrome," American Journal of Medical Genetics Part C (Seminars in Medical Genetics), vol. 163C (2013) (pp. 198-205).
Jeffries, John Lynn. Letter to FDA.
Karkucinska-Wieckowska, et al., "Left Ventricular Noncompaction (LVNC) and Low Mitochondrial Membrane Potential are Specific for Barth Syndrome" J. Inherit. Metab. Dis., Jan. 2013, vol. 36, pp. 929-937.
Koshkin, et al., "Cardiolipin prevents rate-dependent uncoupling and provides osmotic stability in yeast mitochondria," Biochem. J., 2002, vol. 364, pp. 317-322.
Non-Final Office Action in U.S. Appl. No. 16/101,078 dated Mar. 24, 2021.
Non-Final Office Action on U.S. Appl. No. 14/392,293 mailed Jun. 29, 2017.
Non-Final Office Action on U.S. Appl. No. 15/626,255 mailed Apr. 16, 2018.
Non-Final Rejection on U.S. Appl. No. 16/930,028 dated Feb. 25, 2021 (26 pages).
Notice of Allowance in U.S. Appl. No. 14/392,293 dated Apr. 12, 2018.
Notice of Allowance in U.S. Appl. No. 14/771,408 mailed Mar. 1, 2017.
Notice of Allowance on U.S. Appl. No. 15/626,255 DTD May 28, 2021.
Notice of Allowance on U.S. Appl. No. 16/101,078 dated Dec. 22, 2021.
Notice of Refusal in JP Patent Application No. 2015-560380 dated Mar. 22, 2019 (with English translation) (6 pages).
Nurminen et al. "Pathogenicity in POLG syndromes: DNA polymerase gamma pathogenicity prediction server and database," BBA Clinical, vol. 7 (2017) (pp. 147-156).
Office Action in CA Patent Application No. 2916880 dated Jan. 6, 2020.
Office Action in CA Patent Application No. 2916977 dated May 27, 2020 (6 pages).
Office Action in CN Patent Application No. 201480022767.2 dated Mar. 28, 2017 (with English translation).
Office Action in CN Patent Application No. 201480022764.9 dated Jun. 17, 2017.
Office Action in CN Patent Application No. 201480022764.9 dated May 16, 2018.
Office Action in JP Patent Application No. 2015-560380 dated Dec. 25, 2017 (English translation not available).
Office Action in JP Patent Application No. 2015-560380 dated Jun. 1, 2020 (with English translation) (8 pages).
Office Action in JP Patent Application No. 2019-080101 dated Apr. 13, 2020 (with English translation) (7 pages).
Office Action on CA Patent Application No. 2916977 dated Apr. 9, 2021.
Office Action on JP Patent Application No. 2019-133638 dated Jun. 3, 2021 (with English translation) (4 pages).
Palsdottir, et al., "Lipids in membrane protein structures," Biochim Biophys Acta, Nov. 3, 2004, vol. 1666 (1-2), pp. 2-18.
Phoon et al., "Tafazzin knockdown in mice leads to a developmental cardiomyopathy with early diastolic dysfunction preceding myocardial noncompaction," J. Am Heart Assoc, Apr. 2012, vol. 1, No. 2, 13 pages.
Picard, Martin. "Assessment of mitochondrial function in skeletal muscle during disease, disuse and normal aging," Department of Kinesiology and Physical Education, McGill University, Montreal, Canada (2012).
Puccio et al. "Friedreich ataxia: a paradigm for mitochondrial diseases," Curr. Opin. Genetics Develop., 2002, vol. 12, pp. 272-277.
Raja et al. "Barth syndrome: A life-threatening disorder caused by abnormal cardiolipin remodeling," Journal of Rare Diseases Research & Treatment, vol. 2, No. 2 (2017) (pp. 58-62).
Reddy, "Controlled-Release, Pegylation, Liposomal Formulations: New Mechanisms in the Delivery of Injectable Drugs," Ann Pharmacother., Jul./Aug. 2000, vol. 34, pp. 915-923.
Restriction Requirement on U.S. Appl. No. 14/392,293, mailed Oct. 13, 2016.
Ristow et al., "Frataxin activates mitochondrial energy conversion and oxidative phosphorylation," PNAS, Oct. 24, 2000, vol. 97, No. 22, pp. 12239-12243.
Sabbah, Hani N. "Barth syndrome cardiomyopathy: targeting the mitochondria with elamipretide," Heart Failure Reviews (2020) (pp. 1-17).
Sabbah, Hani N. et al., "A canine model of chronic heart failure produced by multiple sequential coronary microembolizations," Am J Physiol.—Heart and Circulatory Physiology, 1991, vol. 260, Issue 4, pp. H1379-H1384.
Saini-Chohan et al. "Cardiolipin biosynthesis and remodeling enzymes are altered during development of heart failure", Journal of Lipid Research vol. 50 (2008) (pp. 1600-1608).
Saneto, et al., "Aplers-Huttenlocher Syndrome," Pediatric Neurol., 2013, vol. 48, pp. 167-178.
Schlame, et al., "Barth syndrome, a human disorder of cardiolipin metabolism," FEBS Letters, 2006, vol. 580, pp. 5450-5455.
Schlame, et al., "The biosynthesis and functional role of cardiolipin," Progress in Lipid Research, 2000, vol. 39, pp. 257-288.
Schulte, et al., "Ataxia with Ophthalmoplegia or Sensory Neuropathy is Frequently caused by POLG Mutations," Neurology, Sep. 15, 2009, vol. 73, No. 11, pp. 898-900.
Second Office Action in CN Patent Application 201480022767.2, No. dated Nov. 9, 2017.
Shoemaker, et al. "Clinically Meaningful Change Estimates for the Six-Minute Walk Test and Daily Activity in Individuals With Chronic Heart Failure," Cardiopulmonary Physical Therapy Journal, vol. 24, No. 3 (2013) (pp. 21-29).
Siegel, et al., "Reversal of Age-Related Mitochondrial Dysfunction in vivo by Treatment with the Mitochondrially Targeted therapeutic SS-31," The FASEB Journal, Apr. 2012, vol. 26, No. 1, 1 page.
Spinazzola, et al., "Clinical and molecular features of mitochondrial DNA depletion syndromes," J. INhert. Metab. Dis., 2009, vol. 32, Issue 2, pp. 143-158.
Stewart, et al., "Novel POLG1 mutations associated with neuromuscular and liver phenotypes in adults and children," J. Med. Genet., Mar. 2009, vol. 46, No. 3, pp. 209-214.
Supplentary Tables. Elamipretide (MPT-131 for SC Injection) (2018).
Takeda, et al., "Barth syndrome diagnosed in the subclinical stage of heart failure based on the presence of lipid storage myopathy and isolated noncompaction of the ventricular myocardium," Eur J Pediatr, 2011, vol. 170, pp. 1481-1484.
Tarnavski, et al., "Mouse cardiac surgery: comprehensive techniques for the generation of mouse models of human diseases and their application for genomic studies," Physiol. Genomics, 2004, vol. 16, Issue 3, pp. 349-360.
The fact sheet of Ataxia Neuropathy Spectrum, retrieved from Genetics Home Reference website, published Feb. 26, 2019, 5 pages.
The fact sheet of Leigh Syndrome, retrieved from the Genetics Home Reference website, published Feb. 21, 2017, 8 pages.
The fact sheet of Progressive External Ophthalmoplegia, retrieved from Genetics Home Reference website, published Feb. 26, 2019, 7 pages.

(56) References Cited

OTHER PUBLICATIONS

The factsheet of Alpers Syndrome from the website of Genetic and Rare Disease Information Center at NIH. (rarediseases.info.nih.gov/diseases/5783/alpers-syndrome), retrieved on Sep. 13, 2021.
The Factsheet of ataxia-neuropathy-spectrum from the MedicinePlus website. (medlineplus.gov/download/genetics/condition/X ataxia-neuropathy-spectrum.pdf).
The Factsheet of Kearns-sayre-syndrome from the NIH website. (rarediseases. info. ni h .gov/diseases/6817 /kearns-sayre-syndrome).
The factsheet of POLG gene from MedicinePlus Website. (medlineplus.gov/download/genetics/gene/polg.pdf).
The factsheet of progressive external ophthalmoplegia (PEO) from the website of Genetic and Rare Disease Information Center at NIH. (rarediseases.info.nih.gov/diseases/4503/chronic-progressive-external-ophthalmoplegia), retrieved on Sep. 13, 2021.
The factsheet of sensory ataxia-neuropathy with dysarthria and ophthalmoparesis (SANDO) from the website of Genetic and Rare w Disease Information Center at NIH. (rarediseases.info.nih.gov/diseases/9998/sensory-ataxic-neuropathy-dysarthria-and-ophthalmoparesis), retrieved on Sep. 13. 2021.
Thompson, et al. "A phase 2/3 randomized clinical trial followed by an open-label extension to evaluate the effectiveness of elamipretide in Barth syndrome, a genetic disorder of mitochondrial cardiolipin metabolism," Genetics in Medicine, vol. 0, No. 0 (2020) (pp. 1-8).
Tiranti, et al., "Mutations of SURF-1 in Leigh Disease Associated with Cytochrome c Oxidase Deficiency," Am. J. Hum. Genet., Dec. 1998, vol. 63, No. 6, pp. 1609-1621.
US Notice of Allowance on U.S. Appl. No. 16/929,370 DTD May 25, 2021.
US Office Action on U.S. Appl. No. 14/392,293 DTD Oct. 13, 2016.
US Office Action on U.S. Appl. No. 16/929,370 DTD Mar. 3, 2021.
Van Goethem, et al., "Mutation of POLG is associated with progressive external ophthalmoplegia characterized by mtDNA deletions," Nature Genetics, Jul. 2001, vol. 28, No. 3, pp. 211-212.
Voller, et al., "Enzyme immunoassays with special reference to ELISA techniques," J. Clinical Pathology, 1978, vol. 31, Issue 6, pp. 507-520.
Weiner, Alan L., "Liposomes for Protein Delivery: Selecting Manufacture and Development Processes," Immunomethods, Jun. 1994, vol. 4, No. 3, pp. 201-209.
Williams, et al., "Cytochrome c Oxidase Subassemblies in Fibroblast Cultures from Patients Carrying Mutations in COX10, SCO1, or SURF1," J. Biol. Chem., 2004, vol. 279, No. 9, pp. 7462-7469.
Wong, et al., "Molecular and Clinical Genetics of Mitochondrial Diseases Due to POLG Mutations," Hum. Mutat., Sep. 200), vol. 29, No. 9, pp. E150-E172.
Zhao et al., "Cell-permeable Peptide Antioxidants Targeted to Inner Mitochondrial Membrane inhibit Mitochondrial Swelling, Oxidative Cell Death, and Reperfusion Injury," The Journal of Biological Chemistry, Aug. 13, 2004, vol. 279, No. 33, pp. 34682-34690.
Zhao, et al., "Transcellular Transport of a Highly Polar 3+ Net Charge Opioid Tetrapeptide," Journal of Pharmacology and Experimental Therapeutics, 2003, vol. 304, No. 1, pp. 425-432.
Zhu, et al., "SURF1, encoding a factor involved in the biogenesis of cytochrome c oxidase, is mutated in Leigh syndrome," Nature Genetics, Dec. 1998, vol. 20, pp. 337-343.
Zou, et al., "An in vitro preliminary study of the radio-protective properties of antioxidant peptide SS31," Journal of Radiation Research and Radiation Proceeding, Oct. 2012, vol. 30, Edition 5, pp. 291-296, (English abstract only).
First Office Action in CN Application No. CN201910589605.1, Dated Nov. 2, 2022, with English-language translation.
Non-Final Office Action on U.S. Appl. No. 17/371,475 dated Jan. 26, 2023 (12 pages).

Sabbah et al., "Acute Intravenous Infusion of Bendavia (MTP-131), A Novel Mitochondria-Targeting Peptide, Improves Left Ventricular Systolic Function in Dogs With Advanced Heart Failure", American Heart Association, Abstract.=, 2012.
Communication pursuant to Article 94(3) EPC on EP Patent Application No. 19190165.1 dated May 9, 2023 (8 pages).
Final Office Action on U.S. Appl. No. 17/371,475, filed May 23, 2023.
Office Action on JP Patent Application No. 2022-077425 dated May 28, 2023 (4 pages) (with English Translation).
Non-Final Office Action on U.S. Appl. No. 18/454,319 dated May 1, 2024.
Office Action in EP 19190165.1, dated Jun. 25, 2024.
Office Action on CA 2916977 dated Aug. 8, 2024.
Nih, "Ataxia neuropathy spectrum," 2021, Retrieved from medlineplus.gov/download/genetics/condition/ataxia-neuropathy-spectrum.pdf.
Nih, "POLG Gene," 2021, Mediline Plus, Retrieved from medlineplus.gov/download/genetics/gene/polg.pdf.
Non-Final Office Action on U.S. Appl. No. 17/963,697 DTD Dec. 4, 2024.
U.S. Appl. No. 18/890,079, filed Sep. 19, 2024, Wilson, T.
Final Office Action on U.S. Appl. No. 18/454,319 DTD Nov. 15, 2024.
Kozarich, et al., "Next generation therapeutics: Looking to the horizon: Editorial overview," Curr. Opin. Chem. Biol., 1998, vol. 2, Issue 4, pp. 439-440.
Lewis et al. "Biological Phenotypes of Heart Failure With Preserved Ejection Fraction," Journal of the American College of Cardiology, vol. 70, No. 17 (2017) (pp. 2186-2200).
Lichtenberg, et al., "Liposomes: Preparation, Characterization, and Preservation," Methods Biochem. Anal., 1998, vol. 33, pp. 337-462.
Liu, et al. "Novel cardiolipin therapeutic protects endothelial mitochondria during renal ischemia and mitigates microvascular rarefaction, inflammation, and fibrosis," American Journal of Physiology-Renal Physiology, vol. 306 (2014) (pp. F970-F980).
Ma, et al., "Superoxide Flashed Early Mitochondrial Signals for Oxidative Stress-Induced Apoptosis" The Journal of Biological Chemistry, 2011, vol. 286, No. 31, pp. 27573-27581.
Ma, et al., "The Human TAZ Gene Complements Mitochondrial Dysfunction in the Yeast taz1? Mutant: Implications for Barth Syndrome," 2004, vol. 279, No. 43, pp. 44394-44399.
Makaryan, et al., "The Cellular and Molecular Mechanisms for Neutropenia in Barth Syndrome" European Journal of Haematology, 2011, vol. 88, pp. 195-209.
Martin, et al., "Leigh syndrome associated with mitochondrial complex I deficiency due to a novel mutation in the NDUFS1 gene," Arch. Neurol., 2005, vol. 62, pp. 659-661.
McHugh, et al., "Sensory ataxic neuropathy dysarthria and ophthalmoparesis (SANDO) in a sibling pair with a homozygous p. A467T POLG mutation," Muscle Nerve, 2010, vol. 41, No. 2, pp. 265-269.
Menezes, et al., "Peripheral neuropathy associated with mitochondrial disease in children," Dev. Med. & Child Neurol. 2012, vol. 54, pp. 407-414.
Mizuguchi, et al., "Intratumor administration of fusogenic liposomes containing fragment A of diphtheria toxin suppresses tumor growth." Cancer Lett., Feb. 26, 1996, vol. 100, Issue 1, pp. 63-69.
Moore et al. "Age-induced mitochondrial DNA point mutations are inadequate to alter metabolic homeostasis in response to nutrient challenge," Aging Cell, vol. 19 (2020) (pp. 1-18).
Non-Final Office Action in U.S. Appl. No. 14/771,408 dated Aug. 10, 2016.
Non-Final Office Action in U.S. Appl. No. 14/771,411 dated Apr. 27, 2017.
Non-Final Office Action in U.S. Appl. No. 14/771,411 dated Mar. 8, 2019, 15 pages.
Non-Final Office Action in U.S. Appl. No. 15/626,255 dated Jan. 23, 2020.
Notice of Allowance on U.S. Appl. No. 18/454,319 DTD Feb. 28, 2025.

METHODS AND COMPOSITIONS FOR DETECTING AND DIAGNOSING DISEASES AND CONDITIONS

CROSS-REFERENCE TO RELATED APPLICATIONS

This application is a continuation of U.S. patent application Ser. No. 16/101,078, filed on Aug. 10, 2018, which is a divisional of U.S. patent application Ser. No. 14/392,293, filed Dec. 23, 2015, which is the U.S. 371 National Stage Application of International Application No. PCT/US2014/043711, filed Jun. 23, 2014, which claims the benefit of and priority to U.S. Provisional Application No. 61/840,760, filed Jun. 28, 2013, and U.S. Provisional Application No. 61/839,753, filed Jun. 26, 2013, the contents of which are hereby incorporated by reference in their entireties.

TECHNICAL FIELD

The present technology relates generally to compositions and methods for detecting and diagnosing diseases and conditions associated with defects in cardiolipin remodeling and/or mitochondrial dysfunction. In particular, the present technology relates to methods for detecting the presence or amount of cardiolipin isoforms and/or the presence or amount of enzymes involved in cardiolipin remodeling.

BACKGROUND

The following description is provided to assist the understanding of the reader. None of the information provided or references cited is admitted to be prior art to the present invention.

Heart failure is a leading cause of mortality and morbidity worldwide. In the United States, it affects nearly 5 million people and is the only major cardiovascular disorder on the rise. It is estimated that 400,000 to 700,000 new cases of heart failure are diagnosed each year in the U.S. and the number of deaths in the U.S. attributable to this condition has more than doubled since 1979, currently averaging 250,000 annually. Although heart failure affects people of all ages, the risk of heart failure increases with age and is most common among older people. Accordingly, the number of people living with heart failure is expected to increase significantly as the elderly population grows over the next few decades. The causes of heart failure have been linked to various disorders including coronary artery disease, atherosclerosis, past myocardial infarction, hypertension, abnormal heart valves, cardiomyopathy or myocarditis, congenital heart disease, severe lung disease, diabetes, severe anemia, hyperthyroidism, arrhythmia or dysrhythmia.

Multiple forms of heart failure are associated with defects in remodeling of the mitochondrial phospholipid cardiolipin, including genetic and sporadic forms of heart failure. Defects in cardiolipin remodeling thus serve as a diagnostic marker for heart failure, which may be monitored via the presence or level of cardiolipin isoforms present in a subject, and/or the presence or level of enzymes involved in cardiolipin remodeling.

SUMMARY

In one aspect, the present disclosure provides a method for diagnosing heart failure in a mammalian subject, the method comprising assessing cardiolipin remodeling in a biological sample from the subject.

In some embodiments, assessing cardiolipin remodeling comprises detecting levels of cardiolipin remodeling enzymes.

In some embodiments, detecting levels of cardiolipin remodeling enzymes comprises detecting the level of one or more of TAZ1, MLCL AT1, or ALCAT1 mRNA compared to a normal control subject.

In some embodiments, the level of MLCL AT1 or ALCAT1 mRNA is elevated about 2.5-fold compared to a normal control subject.

In some embodiments, the level of TAZ1 mRNA is reduced about 2.5-fold compared to a normal control subject.

In some embodiments, assessing cardiolipin remodeling comprises detecting levels of cardiolipin isoforms compared to a normal control subject.

In some embodiments, detecting one or more of TAZ1, MLCL AT1, or ALCAT1 mRNA comprises RT-PCR, in situ hybridization, or Northern blotting.

In some embodiments, detecting levels of cardiolipin isoforms comprises chromatography, mass spectrometry, ELISA, Western blotting, immunodetection, or immunoprecipitation.

In some embodiments, assessing cardiolipin remodeling comprises a mitochondrial function assay.

In some embodiments, the mitochondrial function assay comprises the use of peripheral blood mononuclear cells (PBMCs), leukocytes, or ex vivo tissues.

In some embodiments, the method further comprises administering to the subject a therapeutically effective amount of the peptide D-Arg-2'6'-Dmt-Lys-Phe-NH$_2$ or a pharmaceutically acceptable salt thereof.

In some embodiments, the peptide is administered daily for 6 weeks or more.

In some embodiments, the peptide is administered daily for 12 weeks or more.

In some embodiments, the heart failure results from hypertension; ischemic heart disease; exposure to a cardiotoxic compound; myocarditis; thyroid disease; viral infection; gingivitis; drug abuse; alcohol abuse; pericarditis; atherosclerosis; vascular disease; hypertrophic cardiomyopathy; acute myocardial infarction; left ventricular systolic dysfunction; coronary bypass surgery; starvation; an eating disorder; or a genetic defect.

In some embodiments, the subject is human.

In some embodiments, the peptide is administered orally, topically, systemically, intravenously, subcutaneously, intraperitoneally, or intramuscularly In some embodiments, the method further comprises separately, sequentially or simultaneously administering a cardiovascular agent to the subject.

In some embodiments, the cardiovascular agent is selected from the group consisting of: an anti-arrhythmia agent, a vasodilator, an anti-anginal agent, a corticosteroid, a cardioglycoside, a diuretic, a sedative, an angiotensin converting enzyme (ACE) inhibitor, an angiotensin II antagonist, a thrombolytic agent, a calcium channel blocker, a throboxane receptor antagonist, a radical scavenger, an anti-platelet drug, a β-adrenaline receptor blocking drug, α-receptor blocking drug, a sympathetic nerve inhibitor, a digitalis formulation, an inotrope, and an antihyperlipidemic drug.

In some embodiments, the pharmaceutically acceptable salt comprises acetate or trifluoroacetate salt.

In some embodiments, the biological sample comprises tissue, a cell, or a mitochondria from the subject.

In one aspect, the present disclosure provides a method for monitoring treatment for heart failure in a mammalian subject in need thereof, the method comprising assessing cardiolipin remodeling in a biological sample from the subject.

In some embodiments, assessing cardiolipin remodeling comprises detecting levels of cardiolipin remodeling enzymes.

In some embodiments, detecting levels of cardiolipin remodeling enzymes comprises detecting the level of one or more of TAZ1, MLCL AT1, or ALCAT1 mRNA compared to a normal control subject.

In some embodiments, the level of MLCL AT1 or ALCAT1 mRNA is elevated about 2 to about 2.5-fold compared to a normal control subject.

In some embodiments, the level of TAZ1 mRNA is reduced about 2 to about 2.5-fold compared to a normal control subject.

In some embodiments, assessing cardiolipin remodeling comprises detecting levels of cardiolipin isoforms compared to a normal control subject.

In some embodiments, detecting one or more of TAZ1, MLCL AT1, or ALCAT1 mRNA comprises RT-PCR, in situ hybridization, or Northern blotting.

In some embodiments, detecting levels of cardiolipin isoforms comprises chromatography, mass spectrometry, ELISA, Western blotting, immunodetection, or immunoprecipitation.

In some embodiments, assessing cardiolipin remodeling comprises a mitochondrial function assay.

In some embodiments, the mitochondrial function assay comprises the use of peripheral blood mononuclear cells (PBMCs), leukocytes, or ex vivo tissues.

In some embodiments, the method further comprises administering to the subject a therapeutically effective amount of the peptide D-Arg-2'6'-Dmt-Lys-Phe-NH$_2$ or a pharmaceutically acceptable salt thereof.

In some embodiments, the peptide is administered daily for 6 weeks or more.

In some embodiments, the peptide is administered daily for 12 weeks or more.

In some embodiments, the heart failure results from hypertension; ischemic heart disease; exposure to a cardiotoxic compound; myocarditis; thyroid disease; viral infection; gingivitis; drug abuse; alcohol abuse; pericarditis; atherosclerosis; vascular disease; hypertrophic cardiomyopathy; acute myocardial infarction; left ventricular systolic dysfunction; coronary bypass surgery; starvation; an eating disorder; or a genetic defect.

In some embodiments, the subject is human.

In some embodiments, the peptide is administered orally, topically, systemically, intravenously, subcutaneously, intraperitoneally, or intramuscularly In some embodiments, the method further comprises separately, sequentially or simultaneously administering a cardiovascular agent to the subject.

In some embodiments, the cardiovascular agent is selected from the group consisting of: an anti-arrhythmia agent, a vasodilator, an anti-anginal agent, a corticosteroid, a cardioglycoside, a diuretic, a sedative, an angiotensin converting enzyme (ACE) inhibitor, an angiotensin II antagonist, a thrombolytic agent, a calcium channel blocker, a throboxane receptor antagonist, a radical scavenger, an anti-platelet drug, a β-adrenaline receptor blocking drug, α-receptor blocking drug, a sympathetic nerve inhibitor, a digitalis formulation, an inotrope, and an antihyperlipidemic drug.

In some embodiments, the pharmaceutically acceptable salt comprises acetate or trifluoroacetate salt.

In some embodiments, the biological sample comprises tissue, a cell, or a mitochondria from the subject.

In one aspect, the present disclosure provides a method for assessing mitochondrial dysfunction in a mammalian subject in need thereof, the method comprising assessing cardiolipin remodeling in a biological sample from the subject.

In some embodiments, assessing cardiolipin remodeling comprises detecting levels of cardiolipin remodeling enzymes.

In some embodiments, detecting levels of cardiolipin remodeling enzymes comprises detecting the level of one or more of TAZ1, MLCL AT1, or ALCAT1 mRNA compared to a normal control subject.

In some embodiments, the level of MLCL AT1 or ALCAT1 mRNA is elevated about 2.5-fold compared to a normal control subject.

In some embodiments, the level of TAZ1 mRNA is reduced about 2 to about 2.5-fold compared to a normal control subject.

In some embodiments, assessing cardiolipin remodeling comprises detecting levels of cardiolipin isoforms compared to a normal control subject.

In some embodiments, detecting one or more of TAZ1, MLCL AT1, or ALCAT1 mRNA comprises RT-PCR, in situ hybridization, or Northern blotting.

In some embodiments, detecting levels of cardiolipin isoforms comprises chromatography, mass spectrometry, ELISA, Western blotting, immunodetection, or immunoprecipitation.

In some embodiments, assessing cardiolipin remodeling comprises a mitochondrial function assay.

In some embodiments, the mitochondrial function assay comprises the use of peripheral blood mononuclear cells (PBMCs), leukocytes, or ex vivo tissues.

In some embodiments, the method further comprises administering to the subject a therapeutically effective amount of the peptide D-Arg-2'6'-Dmt-Lys-Phe-NH$_2$ or a pharmaceutically acceptable salt thereof.

In some embodiments, the peptide is administered daily for 6 weeks or more.

In some embodiments, the peptide is administered daily for 12 weeks or more.

In some embodiments, the mitochondrial dysfunction results from hypertension; ischemic heart disease; exposure to a cardiotoxic compound; myocarditis; thyroid disease; viral infection; gingivitis; drug abuse; alcohol abuse; pericarditis; atherosclerosis; vascular disease; hypertrophic cardiomyopathy; acute myocardial infarction; left ventricular systolic dysfunction; coronary bypass surgery; starvation; an eating disorder; or a genetic defect.

In some embodiments, the subject is human.

In some embodiments, the peptide is administered orally, topically, systemically, intravenously, subcutaneously, intraperitoneally, or intramuscularly In some embodiments, the method further comprises separately, sequentially or simultaneously administering a cardiovascular agent to the subject.

In some embodiments, the cardiovascular agent is selected from the group consisting of: an anti-arrhythmia agent, a vasodilator, an anti-anginal agent, a corticosteroid, a cardioglycoside, a diuretic, a sedative, an angiotensin converting enzyme (ACE) inhibitor, an angiotensin II antagonist, a thrombolytic agent, a calcium channel blocker, a throboxane receptor antagonist, a radical scavenger, an anti-platelet drug, a β-adrenaline receptor blocking drug, α-receptor blocking drug, a sympathetic nerve inhibitor, a digitalis formulation, an inotrope, and an antihyperlipidemic drug.

In some embodiments, the pharmaceutically acceptable salt comprises acetate or trifluoroacetate salt.

In some embodiments, the biological sample comprises tissue, a cell, or a mitochondria from the subject.

In one aspect, the present disclosure provides a method for assessing cardiolipin content and composition in a mammalian subject in need thereof, the method comprising assessing cardiolipin remodeling in a biological sample from the subject.

In some embodiments, assessing cardiolipin remodeling comprises detecting levels of cardiolipin remodeling enzymes.

In some embodiments, detecting levels of cardiolipin remodeling enzymes comprises detecting the level of one or more of TAZ1, MLCL AT1, or ALCAT1 mRNA compared to a normal control subject.

In some embodiments, the level of MLCL AT1 or ALCAT1 mRNA is elevated about 2.5-fold compared to a normal control subject.

In some embodiments, the level of TAZ1 mRNA is reduced about 2.5-fold compared to a normal control subject.

In some embodiments, assessing cardiolipin remodeling comprises detecting levels of cardiolipin isoforms compared to a normal control subject.

In some embodiments, detecting one or more of TAZ1, MLCL AT1, or ALCAT1 mRNA comprises RT-PCR, in situ hybridization, or Northern blotting.

In some embodiments, detecting levels of cardiolipin isoforms comprises chromatography, mass spectrometry, ELISA, Western blotting, immunodetection, or immunoprecipitation.

In some embodiments, assessing cardiolipin remodeling comprises a mitochondrial function assay.

In some embodiments, the mitochondrial function assay comprises the use of peripheral blood mononuclear cells (PBMCs), leukocytes, or ex vivo tissues.

In some embodiments, the method further comprises administering to the subject a therapeutically effective amount of the peptide D-Arg-2'6'-Dmt-Lys-Phe-$NH_2$ or a pharmaceutically acceptable salt thereof.

In some embodiments, the peptide is administered daily for 6 weeks or more.

In some embodiments, the peptide is administered daily for 12 weeks or more.

In some embodiments, the cardiolipin content and composition is aberrant due to hypertension; ischemic heart disease; exposure to a cardiotoxic compound; myocarditis; thyroid disease; viral infection; gingivitis; drug abuse; alcohol abuse; pericarditis; atherosclerosis; vascular disease; hypertrophic cardiomyopathy; acute myocardial infarction; left ventricular systolic dysfunction; coronary bypass surgery; starvation; an eating disorder; or a genetic defect.

In some embodiments, the subject is human.

In some embodiments, the peptide is administered orally, topically, systemically, intravenously, subcutaneously, intraperitoneally, or intramuscularly In some embodiments, the method further comprises separately, sequentially or simultaneously administering a cardiovascular agent to the subject.

In some embodiments, the cardiovascular agent is selected from the group consisting of: an anti-arrhythmia agent, a vasodilator, an anti-anginal agent, a corticosteroid, a cardioglycoside, a diuretic, a sedative, an angiotensin converting enzyme (ACE) inhibitor, an angiotensin II antagonist, a thrombolytic agent, a calcium channel blocker, a throboxane receptor antagonist, a radical scavenger, an anti-platelet drug, a β-adrenaline receptor blocking drug, α-receptor blocking drug, a sympathetic nerve inhibitor, a digitalis formulation, an inotrope, and an antihyperlipidemic drug.

In some embodiments, the pharmaceutically acceptable salt comprises acetate or trifluoroacetate salt.

In some embodiments, the biological sample comprises tissue, a cell, or a mitochondria from the subject.

DETAILED DESCRIPTION

It is to be appreciated that certain aspects, modes, embodiments, variations and features of the invention are described below in various levels of detail in order to provide a substantial understanding of the present invention. The definitions of certain terms as used in this specification are provided below. Unless defined otherwise, all technical and scientific terms used herein generally have the same meaning as commonly understood by one of ordinary skill in the art to which this invention belongs.

As used in this specification and the appended claims, the singular forms "a", "an" and "the" include plural referents unless the content clearly dictates otherwise. For example, reference to "a cell" includes a combination of two or more cells, and the like.

As used herein, the "administration" of an agent, drug, or peptide to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein, the term "effective amount" refers to a quantity sufficient to achieve a desired therapeutic and/or prophylactic effect, e.g., an amount which results in the decrease of (e.g., normalization of) expression levels of e.g., MLCL AT 1 or ALCAT1 and/or the increase of (e.g., normalization of) expression levels of e.g., TAZ1 in a subject in need thereof. In the context of therapeutic or prophylactic applications, in some embodiments, the amount of a composition administered to the subject will depend on the type and severity of the disease and on the characteristics of the individual, such as general health, age, sex, body weight and tolerance to drugs. In some embodiments, it will also depend on the degree, severity and type of disease. The skilled artisan will be able to determine appropriate dosages depending on these and other factors. The compositions can also be administered in combination with one or more additional therapeutic compounds. In the methods described herein, the aromatic-cationic peptides may be administered to a subject having one or more signs or symptoms or risk factors of heart failure, such as cardiomegaly, tachypnea, and hepatomegaly. For example, in some embodiments, a "therapeutically effective amount" of the aromatic-cationic peptides includes levels in which the expression of MLCL AT1 or ALCAT1 is reduced in a subject in need thereof after administration. Additionally or alternatively, in some embodiments, a therapeutically effective amount of an aromatic-cationic peptide includes levels in which the expression of TAZ1 is increased in a subject in need thereof after administration. In some embodiments, a therapeutically effective amount also reduces or ameliorates the physiological effects of a heart failure and/or the risk factors of heart failure, and/or the likelihood of heart failure.

As used herein, the term "heart failure" encompasses all forms of heart failure, including but not limited to, e.g., "congestive heart failure" (CHF), "chronic heart failure," and "acute heart failure." As used herein, the term encompasses both sporadic and genetic forms of heart failure. As is known in the art, heart failure is typically characterized by abnormally low cardiac output in which the heart is unable to pump blood at an adequate rate or in adequate volume. When the heart is unable to adequately pump blood to the rest of the body, or when one or more of the heart valves becomes stenotic or otherwise incompetent, blood can back up into the lungs, causing the lungs to become congested with fluid. If this backward flow occurs over an extended period of time, heart failure can result. Typical symptoms of heart failure include shortness of breath (dyspnea), fatigue, weakness, difficulty breathing when lying flat, and swelling of the legs, ankles or abdomen (edema). Causes of heart failure may be related to various disorders including coronary artery disease, systemic hypertension, cardiomyopathy or myocarditis, congenital heart disease, abnormal heart valves or valvular heart disease, severe lung disease, diabetes, severe anemia hyperthyroidism, arrhythmia or dysrhythmia and myocardial infarction. The primary signs of congestive heart failure are cardiomegaly (enlarged heart), tachypnea (rapid breathing; occurs in the case of left side failure) and hepatomegaly (enlarged liver; occurs in the case of right side failure).

As used herein, the term "hypertensive cardiomyopathy" refers to a condition characterized by a weakened heart caused by the effects of hypertension (high blood pressure). Over time, uncontrolled hypertension causes weakness of the heart muscle. As hypertensive cardiomyopathy worsens, it can lead to congestive heart failure. Early symptoms of hypertensive cardiomyopathy include cough, weakness, and fatigue. Additional symptoms of hypertensive cardiomyopathy include leg swelling, weight gain, difficulty breathing when lying flat, increasing shortness of breath with activity, and waking in the middle of the night short of breath.

As used herein, "isolated" or "purified" polypeptide or peptide is substantially free of cellular material or other contaminating polypeptides from the cell or tissue source from which the agent is derived, or substantially free from chemical precursors or other chemicals when chemically synthesized. For example, an isolated aromatic-cationic peptide would be free of materials that would interfere with diagnostic or therapeutic uses of the agent. Such interfering materials may include enzymes, hormones and other proteinaceous and nonproteinaceous solutes.

As used herein, "assessing cardiolipin remodeling" refers to determining whether and to what extent cardiolipin remodeling is defective in a particular subject as compared to a normal control subject. Cardiolipin remodeling may be assessed using methods known in the art as described herein, such as by measuring levels of cardiolipin remodeling enzymes and/or cardiolipin isoforms present in a biological sample from a subject. In some embodiments, the levels of TAZ1, MLCL AT1, or ALCAT1 mRNAs are measured. In some embodiments, the level of the 18:2 cardiolipin isoform is measured. One of skill in the art will understand that cardiolipin remodeling measurements for a particular subject are useful when compared to results for a normal control subject, or in certain contexts, to previous results obtained for the same subject. For example, for methods of diagnosing heart failure, comparison to a normal control subject particularly valuable. For methods of monitoring treatment of heart failure, comparison to results previously obtained for a particular subject, where available, in addition to the normal control subject is valuable.

As used herein, the term "biological sample" refers to a sample from the subject, and includes any bodily fluids, exudates, tissues or cells. Non-limiting examples include blood, plasma, serum, urine, tears, sputum, stool, saliva, nasal swabs, cells such as, but not limited to peripheral blood mononuclear cells (PCMBs), leukocytes, and tissue samples (e.g., biopsie samples). Samples can be fresh, frozen, or otherwise treated or preserved for evaluation by the methods disclosed herein. In some embodiments, levels of TAZ1, MLCL AT1, or ALCAT1 and/or levels and/or isoforms of cardiolipin are determined by assaying a biological sample from a subject.

As used herein, a "normalized" or "normal" expression level (e.g., RNA and/or protein level) of TAZ1, MLCL AT1, or ALCAT1 refers to reducing a subject's MLCL AT1 or ALCAT1 expression level and/or raising a subject's TAZ1 expression level to the subject's baseline expression level or baseline range. Additionally or alternatively, in some embodiments, normalized or normal expression refers to reducing the subject's MLCL AT1 or ALCAT1 expression and/or raising the TAZ1 expression to a level or range determined as "normal" or "control" level, e.g., via control studies and/or control sampling of the subject over time, or of an appropriate population (e.g., matched by age, ethnicity, disease state, drug treatment regime, weight, sex, etc.). As used herein "control level" refers to a level considered average or normal for the subject, or for an appropriate population of subjects.

As used herein "reducing" a subject's MLCL AT1 or ALCAT1 expression level (e.g., RNA and/or protein) means lowering the level of MLCL AT1 or ALCAT1 in the subject (e.g., a subject's MLCL AT1 level in left ventricular myocardium). In some embodiments, reducing MLCL AT1 or ALCAT1 expression level includes a reduction by about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more. Alternatively, or additionally, in some embodiments, reducing MLCL AT1 or ALCAT1 expression level includes a reduction measured as about 1.1 fold to about 1.5 fold reduction, or about 1.5 fold to about 2.0 fold reduction, or about 2.0 fold to about 2.5 fold reduction, or about 2.5 fold to about 3.0 fold reduction.

As used herein "increasing" a subject's TAZ1 expression level means increasing the level of TAZ1 in the subject (e.g., a subject's TAZ1 expression level in left ventricular myocardium). In some embodiments, increasing TAZ1 expression level is an increase by about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or more, e.g., from a baseline or control level. Alternatively, or additionally, in some embodiments, increasing TAZ1 expression level is measured as attenuating the reduction of TAZ1 by about 0.25 fold to about 0.5 fold, or about 0.5 fold to about 0.75 fold, or about 0.75 fold to about 1.0 fold, or about 1.0 fold to about 1.5 fold, e.g., as compared to a baseline or control level.

As used herein, the terms "polypeptide," "peptide," and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art.

As used herein, the term "simultaneous" therapeutic use refers to the administration of at least two active ingredients by the same route and at the same time or at substantially the same time.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the terms "treating" or "treatment" or "alleviation" refers to therapeutic treatment, wherein the object is to reduce or slow down (lessen) or eliminate the targeted pathologic condition or disorder. By way of example, but not by way of limitation, a subject is successfully "treated" for heart failure if, after receiving a therapeutic amount of an aromatic-cationic peptide according to the methods described herein, the subject shows observable and/or measurable reduction in or absence of one or more signs and symptoms of heart failure, such as, e.g., cardiac output, myocardial contractile force, cardiomegaly, tachonea, and/or hepahemogaly. It is also to be appreciated that the various modes of treatment or prevention of medical conditions as described are intended to mean "substantial," which includes total but also less than total treatment or prevention, and wherein some biologically or medically relevant result is achieved. In some embodiments, treating heart failure, as used herein, also refers to treating any one or more of the conditions underlying heart failure, including, without limitation, decreased cardiac contractility, abnormal diastolic compliance, reduced stroke volume, pulmonary congestion, and decreased cardiac output. In some embodiments, "treatment" includes a reduction in MLCL AT1 or ALCAT1 expression and/or an increase in TAZ1 expression in those subjects having higher than a control or "normal" level of MLCL AT1 or ALCAT1 expression and/or a lower than a control or "normal" level of TAZ1.

As used herein, "prevention" or "preventing" of a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. As used herein, preventing heart failure includes preventing the initiation of heart failure, delaying the initiation of heart failure, preventing the progression or advancement of heart failure, slowing the progression or advancement of heart failure, delaying the progression or advancement of heart failure. As used herein, prevention of heart failure also includes preventing a recurrence of heart failure.

Aromatic-Cationic Peptides

The present technology relates to decreasing the expression of MLCL AT1 or ALCAT1 and/or increasing the expression of TAZ1 in a subject in need thereof, by administering aromatic-cationic peptides as disclosed herein. In some embodiments, decreasing the expression of MLCL AT1 or ALCAT1 and/or increasing the expression of TAZ1 is useful for the treatment or prevention of heart failure and related conditions, reducing risk factors associated with heart failure, and/or reducing the likelihood (risk) or severity of heart failure in the subject.

The aromatic-cationic peptides are water-soluble and highly polar. Despite these properties, the peptides can readily penetrate cell membranes. The aromatic-cationic peptides typically include a minimum of three amino acids or a minimum of four amino acids, covalently joined by peptide bonds. The maximum number of amino acids present in the aromatic-cationic peptides is about twenty amino acids covalently joined by peptide bonds. Suitably, the maximum number of amino acids is about twelve, more preferably about nine, and most preferably about six.

The amino acids of the aromatic-cationic peptides can be any amino acid. As used herein, the term "amino acid" is used to refer to any organic molecule that contains at least one amino group and at least one carboxyl group. Typically, at least one amino group is at the α position relative to a carboxyl group. The amino acids may be naturally occurring. Naturally occurring amino acids include, for example, the twenty most common levorotatory (L) amino acids normally found in mammalian proteins, i.e., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan, (Trp), tyrosine (Tyr), and valine (Val). Other naturally occurring amino acids include, for example, amino acids that are synthesized in metabolic processes not associated with protein synthesis. For example, the amino acids ornithine and citrulline are synthesized in mammalian metabolism during the production of urea. Another example of a naturally occurring amino acid includes hydroxyproline (Hyp).

The peptides optionally contain one or more non-naturally occurring amino acids. Optimally, the peptide has no amino acids that are naturally occurring. The non-naturally occurring amino acids may be levorotary (L-), dextrorotatory (D-), or mixtures thereof. Non-naturally occurring amino acids are those amino acids that typically are not synthesized in normal metabolic processes in living organisms, and do not naturally occur in proteins. In addition, the non-naturally occurring amino acids suitably are also not recognized by common proteases. The non-naturally occurring amino acid can be present at any position in the peptide. For example, the non-naturally occurring amino acid can be at the N-terminus, the C-terminus, or at any position between the N-terminus and the C-terminus.

The non-natural amino acids may, for example, comprise alkyl, aryl, or alkylaryl groups not found in natural amino acids. Some examples of non-natural alkyl amino acids include α-aminobutyric acid, β-aminobutyric acid, γ-aminobutyric acid, δ-aminovaleric acid, and ε-aminocaproic acid. Some examples of non-natural aryl amino acids include ortho-, meta-, and para-aminobenzoic acid. Some examples of non-natural alkylaryl amino acids include ortho-, meta-, and para-aminophenylacetic acid, and γ-phenyl-β-aminobutyric acid. Non-naturally occurring amino acids include derivatives of naturally occurring amino acids. The derivatives of naturally occurring amino acids may, for example, include the addition of one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include branched or unbranched $C_1$-$C_4$ alkyl, such as methyl, ethyl, n-propyl, isopropyl, butyl, isobutyl, or t-butyl, $C_1$-$C_4$ alkyloxy (i.e., alkoxy), amino, $C_1$-$C_4$ alkylamino and $C_1$-$C_4$ dialkylamino (e.g., methylamino, dimethylamino), nitro, hydroxyl, halo (i.e., fluoro, chloro, bromo, or iodo). Some specific examples of non-naturally occurring derivatives of naturally occurring amino acids include norvaline (Nva) and norleucine (Nle).

Another example of a modification of an amino acid in a peptide is the derivatization of a carboxyl group of an aspartic acid or a glutamic acid residue of the peptide. One example of derivatization is amidation with ammonia or with a primary or secondary amine, e.g. methylamine, ethylamine, dimethylamine or diethylamine. Another example of derivatization includes esterification with, for example, methyl or ethyl alcohol. Another such modification includes derivatization of an amino group of a lysine, arginine, or histidine residue. For example, such amino groups can be acylated. Some suitable acyl groups include, for example, a benzoyl group or an alkanoyl group comprising any of the $C_1$-$C_4$ alkyl groups mentioned above, such as an acetyl or propionyl group.

The non-naturally occurring amino acids are suitably resistant or insensitive to common proteases. Examples of non-naturally occurring amino acids that are resistant or insensitive to proteases include the dextrorotatory (D-) form of any of the above-mentioned naturally occurring L-amino acids, as well as L- and/or D-non-naturally occurring amino acids. The D-amino acids do not normally occur in proteins, although they are found in certain peptide antibiotics that are synthesized by means other than the normal ribosomal protein synthetic machinery of the cell. As used herein, the D-amino acids are considered to be non-naturally occurring amino acids.

In order to minimize protease sensitivity, the peptides should have less than five, preferably less than four, more preferably less than three, and most preferably, less than two contiguous L-amino acids recognized by common proteases, irrespective of whether the amino acids are naturally or non-naturally occurring. Optimally, the peptide has only D-amino acids, and no L-amino acids. If the peptide contains protease sensitive sequences of amino acids, at least one of the amino acids is preferably a non-naturally-occurring D-amino acid, thereby conferring protease resistance. An example of a protease sensitive sequence includes two or more contiguous basic amino acids that are readily cleaved by common proteases, such as endopeptidases and trypsin. Examples of basic amino acids include arginine, lysine and histidine.

The aromatic-cationic peptides should have a minimum number of net positive charges at physiological pH in comparison to the total number of amino acid residues in the peptide. The minimum number of net positive charges at physiological pH will be referred to below as ($p_m$). The total number of amino acid residues in the peptide will be referred to below as (r). The minimum number of net positive charges discussed below are all at physiological pH. The term "physiological pH" as used herein refers to the normal pH in the cells of the tissues and organs of the mammalian body. For instance, the physiological pH of a human is normally approximately 7.4, but normal physiological pH in mammals may be any pH from about 7.0 to about 7.8.

"Net charge" as used herein refers to the balance of the number of positive charges and the number of negative charges carried by the amino acids present in the peptide. In this specification, it is understood that net charges are measured at physiological pH. The naturally occurring amino acids that are positively charged at physiological pH include L-lysine, L-arginine, and L-histidine. The naturally occurring amino acids that are negatively charged at physiological pH include L-aspartic acid and L-glutamic acid.

Typically, a peptide has a positively charged N-terminal amino group and a negatively charged C-terminal carboxyl group. The charges cancel each other out at physiological pH. As an example of calculating net charge, the peptide Tyr-Arg-Phe-Lys-Glu-His-Trp-D-Arg has one negatively charged amino acid (i.e., Glu) and four positively charged amino acids (i.e., two Arg residues, one Lys, and one His). Therefore, the above peptide has a net positive charge of three.

In one embodiment, the aromatic-cationic peptides have a relationship between the minimum number of net positive charges at physiological pH ($p_m$) and the total number of amino acid residues (r) wherein $3p_m$ is the largest number that is less than or equal to r+1. In this embodiment, the relationship between the minimum number of net positive charges ($p_m$) and the total number of amino acid residues (r) is as follows:

TABLE 1

| Amino acid number and net positive charges ($3p_m \leq p + 1$) | | | | | | | | | | | | | | | | | | |
|---|---|---|---|---|---|---|---|---|---|---|---|---|---|---|---|---|---|---|
| (r) | 3 | 4 | 5 | 6 | 7 | 8 | 9 | 10 | 11 | 12 | 13 | 14 | 15 | 16 | 17 | 18 | 19 | 20 |
| ($p_m$) | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of net positive charges ($p_m$) and the total number of amino acid residues (r) wherein $2p_m$ is the largest number that is less than or equal to r+1. In this embodiment, the relationship between the minimum number of net positive charges ($p_m$) and the total number of amino acid residues (r) is as follows:

TABLE 2

Amino acid number and net positive charges ($2p_m \leq p + 1$)

| (r) | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|
| ($p_m$) | 2 | 2 | 3 | 3 | 4 | 4 | 5 | 5 | 6 | 6 | 7 | 7 | 8 | 8 | 9 | 9 | 10 | 10 |

In one embodiment, the minimum number of net positive charges ($p_m$) and the total number of amino acid residues (r) are equal. In another embodiment, the peptides have three or four amino acid residues and a minimum of one net positive charge, suitably, a minimum of two net positive charges and more preferably a minimum of three net positive charges.

It is also important that the aromatic-cationic peptides have a minimum number of aromatic groups in comparison to the total number of net positive charges ($p_t$). The minimum number of aromatic groups will be referred to below as (a). Naturally occurring amino acids that have an aromatic group include the amino acids histidine, tryptophan, tyrosine, and phenylalanine. For example, the hexapeptide Lys-Gln-Tyr-D-Arg-Phe-Trp has a net positive charge of two (contributed by the lysine and arginine residues) and three aromatic groups (contributed by tyrosine, phenylalanine and tryptophan residues).

The aromatic-cationic peptides should also have a relationship between the minimum number of aromatic groups (a) and the total number of net positive charges at physiological pH ($p_t$) wherein 3a is the largest number that is less than or equal to $p_t$+1, except that when $p_t$ is 1, a may also be 1. In this embodiment, the relationship between the minimum number of aromatic groups (a) and the total number of net positive charges ($p_t$) is as follows:

TABLE 3

Aromatic groups and net positive charges ($3a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 1 | 1 | 2 | 2 | 2 | 3 | 3 | 3 | 4 | 4 | 4 | 5 | 5 | 5 | 6 | 6 | 6 | 7 |

In another embodiment, the aromatic-cationic peptides have a relationship between the minimum number of aromatic groups (a) and the total number of net positive charges ($p_t$) wherein 2a is the largest number that is less than or equal to $p_t$+1. In this embodiment, the relationship between the minimum number of aromatic amino acid residues (a) and the total number of net positive charges ($p_t$) is as follows:

TABLE 4

Aromatic groups and net positive charges ($2a \leq p_t + 1$ or $a = p_t = 1$)

| ($p_t$) | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| (a) | 1 | 1 | 2 | 2 | 3 | 3 | 4 | 4 | 5 | 5 | 6 | 6 | 7 | 7 | 8 | 8 | 9 | 9 | 10 | 10 |

In another embodiment, the number of aromatic groups (a) and the total number of net positive charges ($p_t$) are equal.

Carboxyl groups, especially the terminal carboxyl group of a C-terminal amino acid, are suitably amidated with, for example, ammonia to form the C-terminal amide. Alternatively, the terminal carboxyl group of the C-terminal amino acid may be amidated with any primary or secondary amine. The primary or secondary amine may, for example, be an alkyl, especially a branched or unbranched $C_1$-$C_4$ alkyl, or an aryl amine. Accordingly, the amino acid at the C-terminus of the peptide may be converted to an amido, N-methylamido, N-ethylamido, N,N-dimethylamido, N,N-diethylamido, N-methyl-N-ethylamido, N-phenylamido or N-phenyl-N-ethylamido group. The free carboxylate groups of the asparagine, glutamine, aspartic acid, and glutamic acid residues not occurring at the C-terminus of the aromatic-cationic peptides may also be amidated wherever they occur within the peptide. The amidation at these internal positions may be with ammonia or any of the primary or secondary amines described above.

In one embodiment, the aromatic-cationic peptide is a tripeptide having two net positive charges and at least one aromatic amino acid. In a particular embodiment, the aromatic-cationic peptide is a tripeptide having two net positive charges and two aromatic amino acids.

Aromatic-cationic peptides include, but are not limited to, the following peptide examples:

TABLE 5

EXEMPLARY PEPTIDES

2',6'-Dmp-D-Arg-2',6'-Dmt-Lys-NH$_2$

2',6'-Dmp-D-Arg-Phe-Lys-NH$_2$

2',6'-Dmt-D-Arg-PheOrn-NH$_2$

2',6'-Dmt-D-Arg-Phe-Ahp(2-aminoheptanoicacid)-NH$_2$

2',6'-Dmt-D-Arg-Phe-Lys-NH$_2$

2',6'-Dmt-D-Cit-PheLys-NH$_2$

Ala-D-Phe-D-Arg-Tyr-Lys-D-Trp-His-D-Tyr-Gly-Phe

Arg-D-Leu-D-Tyr-Phe-Lys-Glu-D-Lys-Arg-D-Trp-Lys-D-Phe-Tyr-D-Arg-Gly

Asp-Arg-D-Phe-Cys-Phe-D-Arg-D-Lys-Tyr-Arg-D-Tyr-Trp-D-His-Tyr-D-Phe-Lys-Phe

Asp-D-Trp-Lys-Tyr-D-His-Phe-Arg-D-Gly-Lys-NH$_2$

D-Arg-2',6'-Dmt-Lys-Phe-NH$_2$

D-Glu-Asp-Lys-D-Arg-D-His-Phe-Phe-D-Val-Tyr-Arg-Tyr-D-Tyr-Arg-His-Phe-NH$_2$

D-His-Glu-Lys-Tyr-D-Phe-Arg

D-His-Lys-Tyr-D-Phe-Glu-D-Asp-D-Asp-D-His-D-Lys-Arg-Trp-NH$_2$

D-Tyr-Trp-Lys-NH$_2$

Glu-Arg-D-Lys-Tyr-D-Val-Phe-D-His-Trp-Arg-D-Gly-Tyr-Arg-D-Met-NH$_2$

Gly-Ala-Lys-Phe-D-Lys-Glu-Arg-Tyr-His-D-Arg-D-Arg-Asp-Tyr-Trp-D-His-Trp-His-D-Lys-Asp.

Gly-D-Phe-Lys-His-D-Arg-Tyr-NH$_2$

His-Tyr-D-Arg-Trp-Lys-Phe-D-Asp-Ala-Arg-Cys-D-Tyr-His-Phe-D-Lys-Tyr-His-Ser-NH$_2$

Lys-D-Arg-Tyr-NH$_2$

Lys-D-Gln-Tyr-Arg-D-Phe-Trp-NH$_2$

Lys-Trp-D-Tyr-Arg-Asn-Phe-Tyr-D-His-NH$_2$

Met-Tyr-D-Arg-Phe-Arg-NH$_2$

Met-Tyr-D-Lys-Phe-Arg

Phe-Arg-D-His-Asp

Phe-D-Arg-2',6'-Dmt-Lys-NH$_2$

Phe-D-Arg-His

Phe-D-Arg-Lys-Trp-Tyr-D-Arg-His

Phe-D-Arg-Phe-Lys-NH$_2$

Phe-Phe-D-Tyr-Arg-Glu-Asp-D-Lys-Arg-D-Arg-His-Phe-NH$_2$

Phe-Tyr-Lys-D-Arg-Trp-His-D-Lys-D-Lys-Glu-Arg-D-Tyr-Thr

Thr-Gly-Tyr-Arg-D-His-Phe-Trp-D-His-Lys

Thr-Tyr-Arg-D-Lys-Trp-Tyr-Glu-Asp-D-Lys-D-Arg-His-Phe-D-Tyr-Gly-Val-Ile-D-His-Arg-Tyr-Lys-NH$_2$

Trp-D-Lys-Tyr-Arg-NH$_2$

TABLE 5-continued

EXEMPLARY PEPTIDES

Trp-Lys-Phe-D-Asp-Arg-Tyr-D-His-Lys

Tyr-Asp-D-Lys-Tyr-Phe-D-Lys-D-Arg-Phe-Pro-D-Tyr-His-Lys

Tyr-D-Arg-Phe-Lys-Glu-NH$_2$

Tyr-D-Arg-Phe-Lys-NH$_2$

Tyr-D-His-Phe-D-Arg-Asp-Lys-D-Arg-His-Trp-D-His-Phe

Tyr-His-D-Gly-Met

Val-D-Lys-His-Tyr-D-Phe-Ser-Tyr-Arg-NH$_2$

In one embodiment, the peptides have mu-opioid receptor agonist activity (i.e., they activate the mu-opioid receptor). Peptides, which have mu-opioid receptor agonist activity, are typically those peptides that have a tyrosine residue or a tyrosine derivative at the N-terminus (i.e., the first amino acid position). Suitable derivatives of tyrosine include 2'-methyltyrosine (Mmt); 2',6'-dimethyltyrosine (2'6'-Dmt); 3',5'-dimethyltyrosine (3'5'Dmt); N,2',6'-trimethyltyrosine (Tmt); and 2'-hydroxy-6'-methyltryosine (Hmt).

In one embodiment, a peptide that has mu-opioid receptor agonist activity has the formula Tyr-D-Arg-Phe-Lys-NH$_2$. Tyr-D-Arg-Phe-Lys-NH$_2$ has a net positive charge of three, contributed by the amino acids tyrosine, arginine, and lysine and has two aromatic groups contributed by the amino acids phenylalanine and tyrosine. The tyrosine of Tyr-D-Arg-Phe-Lys-NH$_2$ can be a modified derivative of tyrosine such as in 2',6'-dimethyltyrosine to produce the compound having the formula 2',6'-Dmt-D-Arg-Phe-Lys-NH$_2$. 2',6'-Dmt-D-Arg-Phe-Lys-NH$_2$ has a molecular weight of 640 and carries a net three positive charge at physiological pH. 2',6'-Dmt-D-Arg-Phe-Lys-NH$_2$ readily penetrates the plasma membrane of several mammalian cell types in an energy-independent manner (Zhao et al., *J. Pharmacol Exp Ther.,* 304:425-432, 2003).

Alternatively, in other instances, the aromatic-cationic peptide does not have mu-opioid receptor agonist activity. For example, during long-term treatment, such as in a chronic disease state or condition, the use of an aromatic-cationic peptide that activates the mu-opioid receptor may be contraindicated. In these instances, the potentially adverse or addictive effects of the aromatic-cationic peptide may preclude the use of an aromatic-cationic peptide that activates the mu-opioid receptor in the treatment regimen of a human patient or other mammal. Potential adverse effects may include sedation, constipation and respiratory depression. In such instances an aromatic-cationic peptide that does not activate the mu-opioid receptor may be an appropriate treatment. Peptides that do not have mu-opioid receptor agonist activity generally do not have a tyrosine residue or a derivative of tyrosine at the N-terminus (i.e., amino acid position 1). The amino acid at the N-terminus can be any naturally occurring or non-naturally occurring amino acid other than tyrosine. In one embodiment, the amino acid at the N-terminus is phenylalanine or its derivative. Exemplary derivatives of phenylalanine include 2'-methylphenylalanine (Mmp), 2',6'-dimethylphenylalanine (2',6'-Dmp), N,2',6'-trimethylphenylalanine (Tmp), and 2'-hydroxy-6'-methylphenylalanine (Hmp).

An example of an aromatic-cationic peptide that does not have mu-opioid receptor agonist activity has the formula Phe-D-Arg-Phe-Lys-NH$_2$. Alternatively, the N-terminal phenylalanine can be a derivative of phenylalanine such as 2',6'-dimethylphenylalanine (2'6'-Dmp). Tyr-D-Arg-Phe-Lys-NH$_2$ containing 2',6'-dimethylphenylalanine at amino acid position 1 has the formula 2',6'-Dmp-D-Arg-Phe-Lys-NH$_2$. In one embodiment, the amino acid sequence of 2',6'-Dmt-D-Arg-Phe-Lys-NH$_2$ is rearranged such that Dmt is not at the N-terminus. An example of such an aromatic-cationic peptide that does not have mu-opioid receptor agonist activity has the formula D-Arg-2'6'-Dmt-Lys-Phe-NH$_2$.

Suitable substitution variants of the peptides listed herein include conservative amino acid substitutions. Amino acids may be grouped according to their physicochemical characteristics as follows:

(a) Non-polar amino acids: Ala(A) Ser(S) Thr(T) Pro(P) Gly(G) Cys (C);
(b) Acidic amino acids: Asn(N) Asp(D) Glu(E) Gln(Q);
(c) Basic amino acids: His(H) Arg(R) Lys(K);
(d) Hydrophobic amino acids: Met(M) Leu(L) Ile(I) Val (V); and
(e) Aromatic amino acids: Phe(F) Tyr(Y) Trp(W) His (H).

Substitutions of an amino acid in a peptide by another amino acid in the same group is referred to as a conservative substitution and may preserve the physicochemical characteristics of the original peptide. In contrast, substitutions of an amino acid in a peptide by another amino acid in a different group is generally more likely to alter the characteristics of the original peptide.

Examples of peptides that activate mu-opioid receptors include, but are not limited to, the aromatic-cationic peptides shown in Table 6.

TABLE 6

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Tyr | D-Arg | Phe | Lys | NH$_2$ |
| Tyr | D-Arg | Phe | Orn | NH$_2$ |
| Tyr | D-Arg | Phe | Dab | NH$_2$ |
| Tyr | D-Arg | Phe | Dap | NH$_2$ |
| 2'6'Dmt | D-Arg | Phe | Lys | NH$_2$ |
| 2'6'Dmt | D-Arg | Phe | Lys-NH(CH$_2$)$_2$—NH-dns | NH$_2$ |
| 2'6'Dmt | D-Arg | Phe | Lys-NH(CH$_2$)$_2$—NH-atn | NH$_2$ |
| 2'6'Dmt | D-Arg | Phe | dnsLys | NH$_2$ |
| 2'6'Dmt | D-Cit | Phe | Lys | NH$_2$ |
| 2'6'Dmt | D-Cit | Phe | Ahp | NH$_2$ |
| 2'6'Dmt | D-Arg | Phe | Orn | NH$_2$ |
| 2'6'Dmt | D-Arg | Phe | Dab | NH$_2$ |
| 2'6'Dmt | D-Arg | Phe | Dap | NH$_2$ |
| 2'6'Dmt | D-Arg | Phe | Ahp(2-aminoheptanoic acid) | NH$_2$ |
| Bio-2'6'Dmt | D-Arg | Phe | Lys | NH$_2$ |
| 3'5'Dmt | D-Arg | Phe | Lys | NH$_2$ |
| 3'5'Dmt | D-Arg | Phe | Orn | NH$_2$ |
| 3'5'Dmt | D-Arg | Phe | Dab | NH$_2$ |
| 3'5'Dmt | D-Arg | Phe | Dap | NH$_2$ |
| Tyr | D-Arg | Tyr | Lys | NH$_2$ |
| Tyr | D-Arg | Tyr | Orn | NH$_2$ |
| Tyr | D-Arg | Tyr | Dab | NH$_2$ |
| Tyr | D-Arg | Tyr | Dap | NH$_2$ |
| 2'6'Dmt | D-Arg | Tyr | Lys | NH$_2$ |
| 2'6'Dmt | D-Arg | Tyr | Orn | NH$_2$ |
| 2'6'Dmt | D-Arg | Tyr | Dab | NH$_2$ |
| 2'6'Dmt | D-Arg | Tyr | Dap | NH$_2$ |
| 2'6'Dmt | D-Arg | 2'6'Dmt | Lys | NH$_2$ |
| 2'6'Dmt | D-Arg | 2'6'Dmt | Orn | NH$_2$ |
| 2'6'Dmt | D-Arg | 2'6'Dmt | Dab | NH$_2$ |
| 2'6'Dmt | D-Arg | 2'6'Dmt | Dap | NH$_2$ |
| 3'5'Dmt | D-Arg | 3'5'Dmt | Arg | NH$_2$ |
| 3'5'Dmt | D-Arg | 3'5'Dmt | Lys | NH$_2$ |
| 3'5'Dmt | D-Arg | 3'5'Dmt | Orn | NH$_2$ |
| 3'5'Dmt | D-Arg | 3'5'Dmt | Dab | NH$_2$ |
| Tyr | D-Lys | Phe | Dap | NH$_2$ |
| Tyr | D-Lys | Phe | Arg | NH$_2$ |
| Tyr | D-Lys | Phe | Lys | NH$_2$ |
| Tyr | D-Lys | Phe | Orn | NH$_2$ |
| 2'6'Dmt | D-Lys | Phe | Dab | NH$_2$ |
| 2'6'Dmt | D-Lys | Phe | Dap | NH$_2$ |
| 2'6'Dmt | D-Lys | Phe | Arg | NH$_2$ |
| 2'6'Dmt | D-Lys | Phe | Lys | NH$_2$ |
| 3'5'Dmt | D-Lys | Phe | Orn | NH$_2$ |
| 3'5'Dmt | D-Lys | Phe | Dab | NH$_2$ |
| 3'5'Dmt | D-Lys | Phe | Dap | NH$_2$ |
| 3'5'Dmt | D-Lys | Phe | Arg | NH$_2$ |
| Tyr | D-Lys | Tyr | Lys | NH$_2$ |
| Tyr | D-Lys | Tyr | Orn | NH$_2$ |
| Tyr | D-Lys | Tyr | Dab | NH$_2$ |
| Tyr | D-Lys | Tyr | Dap | NH$_2$ |
| 2'6'Dmt | D-Lys | Tyr | Lys | NH$_2$ |
| 2'6'Dmt | D-Lys | Tyr | Orn | NH$_2$ |
| 2'6'Dmt | D-Lys | Tyr | Dab | NH$_2$ |
| 2'6'Dmt | D-Lys | Tyr | Dap | NH$_2$ |
| 2'6'Dmt | D-Lys | 2'6'Dmt | Lys | NH$_2$ |
| 2'6'Dmt | D-Lys | 2'6'Dmt | Orn | NH$_2$ |
| 2'6'Dmt | D-Lys | 2'6'Dmt | Dab | NH$_2$ |
| 2'6'Dmt | D-Lys | 2'6'Dmt | Dap | NH$_2$ |
| 2'6'Dmt | D-Arg | Phe | dnsDap | NH$_2$ |
| 2'6'Dmt | D-Arg | Phe | atnDap | NH$_2$ |
| 3'5'Dmt | D-Lys | 3'5'Dmt | Lys | NH$_2$ |
| 3'5'Dmt | D-Lys | 3'5'Dmt | Orn | NH$_2$ |
| 3'5'Dmt | D-Lys | 3'5'Dmt | Dab | NH$_2$ |
| 3'5'Dmt | D-Lys | 3'5'Dmt | Dap | NH$_2$ |
| Tyr | D-Lys | Phe | Arg | NH$_2$ |
| Tyr | D-Orn | Phe | Arg | NH$_2$ |
| Tyr | D-Dab | Phe | Arg | NH$_2$ |
| Tyr | D-Dap | Phe | Arg | NH$_2$ |
| 2'6'Dmt | D-Arg | Phe | Arg | NH$_2$ |
| 2'6'Dmt | D-Lys | Phe | Arg | NH$_2$ |
| 2'6'Dmt | D-Orn | Phe | Arg | NH$_2$ |
| 2'6'Dmt | D-Dab | Phe | Arg | NH$_2$ |
| 3'5'Dmt | D-Dap | Phe | Arg | NH$_2$ |
| 3'5'Dmt | D-Arg | Phe | Arg | NH$_2$ |
| 3'5'Dmt | D-Lys | Phe | Arg | NH$_2$ |
| 3'5'Dmt | D-Orn | Phe | Arg | NH$_2$ |
| Tyr | D-Lys | Tyr | Arg | NH$_2$ |
| Tyr | D-Orn | Tyr | Arg | NH$_2$ |
| Tyr | D-Dab | Tyr | Arg | NH$_2$ |
| Tyr | D-Dap | Tyr | Arg | NH$_2$ |
| 2'6'Dmt | D-Arg | 2'6'Dmt | Arg | NH$_2$ |
| 2'6'Dmt | D-Lys | 2'6'Dmt | Arg | NH$_2$ |
| 2'6'Dmt | D-Orn | 2'6'Dmt | Arg | NH$_2$ |
| 2'6'Dmt | D-Dab | 2'6'Dmt | Arg | NH$_2$ |
| 3'5'Dmt | D-Dap | 3'5'Dmt | Arg | NH$_2$ |
| 3'5'Dmt | D-Arg | 3'5'Dmt | Arg | NH$_2$ |
| 3'5'Dmt | D-Lys | 3'5'Dmt | Arg | NH$_2$ |
| 3'5'Dmt | D-Orn | 3'5'Dmt | Arg | NH$_2$ |
| Mmt | D-Arg | Phe | Lys | NH$_2$ |
| Mmt | D-Arg | Phe | Orn | NH$_2$ |
| Mmt | D-Arg | Phe | Dab | NH$_2$ |
| Mmt | D-Arg | Phe | Dap | NH$_2$ |
| Tmt | D-Arg | Phe | Lys | NH$_2$ |
| Tmt | D-Arg | Phe | Orn | NH$_2$ |
| Tmt | D-Arg | Phe | Dab | NH$_2$ |
| Tmt | D-Arg | Phe | Dap | NH$_2$ |
| Hmt | D-Arg | Phe | Lys | NH$_2$ |
| Hmt | D-Arg | Phe | Orn | NH$_2$ |
| Hmt | D-Arg | Phe | Dab | NH$_2$ |
| Hmt | D-Arg | Phe | Dap | NH$_2$ |
| Mmt | D-Lys | Phe | Lys | NH$_2$ |
| Mmt | D-Lys | Phe | Orn | NH$_2$ |

TABLE 6-continued

Peptide Analogs with Mu-Opioid Activity

| Amino Acid Position 1 | Amino Acid Position 2 | Amino Acid Position 3 | Amino Acid Position 4 | C-Terminal Modification |
|---|---|---|---|---|
| Mmt | D-Lys | Phe | Dab | $NH_2$ |
| Mmt | D-Lys | Phe | Dap | $NH_2$ |
| Mmt | D-Lys | Phe | Arg | $NH_2$ |
| Tmt | D-Lys | Phe | Lys | $NH_2$ |
| Tmt | D-Lys | Phe | Orn | $NH_2$ |
| Tmt | D-Lys | Phe | Dab | $NH_2$ |
| Tmt | D-Lys | Phe | Dap | $NH_2$ |
| Tmt | D-Lys | Phe | Arg | $NH_2$ |
| Hmt | D-Lys | Phe | Lys | $NH_2$ |
| Hmt | D-Lys | Phe | Orn | $NH_2$ |
| Hmt | D-Lys | Phe | Dab | $NH_2$ |
| Hmt | D-Lys | Phe | Dap | $NH_2$ |
| Hmt | D-Lys | Phe | Arg | $NH_2$ |
| Mmt | D-Lys | Phe | Arg | $NH_2$ |
| Mmt | D-Orn | Phe | Arg | $NH_2$ |
| Mmt | D-Dab | Phe | Arg | $NH_2$ |
| Mmt | D-Dap | Phe | Arg | $NH_2$ |
| Mmt | D-Arg | Phe | Arg | $NH_2$ |
| Tmt | D-Lys | Phe | Arg | $NH_2$ |
| Tmt | D-Orn | Phe | Arg | $NH_2$ |
| Tmt | D-Dab | Phe | Arg | $NH_2$ |
| Tmt | D-Dap | Phe | Arg | $NH_2$ |
| Tmt | D-Arg | Phe | Arg | $NH_2$ |
| Hmt | D-Lys | Phe | Arg | $NH_2$ |
| Hmt | D-Orn | Phe | Arg | $NH_2$ |
| Hmt | D-Dab | Phe | Arg | $NH_2$ |
| Hmt | D-Dap | Phe | Arg | $NH_2$ |
| Hmt | D-Arg | Phe | Arg | $NH_2$ |

Dab = diaminobutyric
Dap = diaminopropionic acid
Dmt = dimethyltyrosine
Mmt = 2'-methyltyrosine
Tmt = N,2',6'-trimethyltyrosine
Hmt = 2'-hydroxy,6'-methyltyrosine
dnsDap = β-dansyl-L-α,β-diaminopropionic acid
atnDap = β-anthraniloyl-L-α,β-diaminopropionic acid
Bio = biotin Examples of peptides that do not activate mu-opioid receptors include, but are not limited to, the aromatic-cationic peptides shown in Table 7.

TABLE 7

Peptide Analogs Lacking Mu-Opioid Activity

| Amino Acid Position 1 | Amino Acid Position 2 | Amino Acid Position 3 | Amino Acid Position 4 | C-Terminal Modification |
|---|---|---|---|---|
| D-Arg | Dmt | Lys | Phe | $NH_2$ |
| D-Arg | Dmt | Phe | Lys | $NH_2$ |
| D-Arg | Phe | Lys | Dmt | $NH_2$ |
| D-Arg | Phe | Dmt | Lys | $NH_2$ |
| D-Arg | Lys | Dmt | Phe | $NH_2$ |
| D-Arg | Lys | Phe | Dmt | $NH_2$ |
| Phe | Lys | Dmt | D-Arg | $NH_2$ |
| Phe | Lys | D-Arg | Dmt | $NH_2$ |
| Phe | D-Arg | Phe | Lys | $NH_2$ |
| Phe | D-Arg | Dmt | Lys | $NH_2$ |
| Phe | D-Arg | Lys | Dmt | $NH_2$ |
| Phe | Dmt | D-Arg | Lys | $NH_2$ |
| Phe | Dmt | Lys | D-Arg | $NH_2$ |
| Lys | Phe | D-Arg | Dmt | $NH_2$ |
| Lys | Phe | Dmt | D-Arg | $NH_2$ |
| Lys | Dmt | D-Arg | Phe | $NH_2$ |
| Lys | Dmt | Phe | D-Arg | $NH_2$ |
| Lys | D-Arg | Phe | Dmt | $NH_2$ |
| Lys | D-Arg | Dmt | Phe | $NH_2$ |
| D-Arg | Dmt | D-Arg | Phe | $NH_2$ |
| D-Arg | Dmt | D-Arg | Dmt | $NH_2$ |
| D-Arg | Dmt | D-Arg | Tyr | $NH_2$ |
| D-Arg | Dmt | D-Arg | Trp | $NH_2$ |
| Trp | D-Arg | Phe | Lys | $NH_2$ |
| Trp | D-Arg | Tyr | Lys | $NH_2$ |
| Trp | D-Arg | Trp | Lys | $NH_2$ |
| Trp | D-Arg | Dmt | Lys | $NH_2$ |
| D-Arg | Trp | Lys | Phe | $NH_2$ |
| D-Arg | Trp | Phe | Lys | $NH_2$ |
| D-Arg | Trp | Lys | Dmt | $NH_2$ |
| D-Arg | Trp | Dmt | Lys | $NH_2$ |
| D-Arg | Lys | Trp | Phe | $NH_2$ |
| D-Arg | Lys | Trp | Dmt | $NH_2$ |
| Cha | D-Arg | Phe | Lys | $NH_2$ |
| Ala | D-Arg | Phe | Lys | $NH_2$ |

Cha = cyclohexyl alanine

The amino acids of the peptides shown in the tables above may be in either the L- or the D-configuration.

The peptides may be synthesized by any of the methods well known in the art. Suitable methods for chemically synthesizing the protein include, for example, those described by Stuart and Young in *Solid Phase Peptide Synthesis*, Second Edition, Pierce Chemical Company (1984), and in *Methods Enzymol.*, 289, Academic Press, Inc, New York (1997).

Cardiolipin Remodeling

Cardiolipin (cardiolipin) is an important component of the inner mitochondrial membrane, where it constitutes about 20% of the total lipid composition. In mammalian cells, cardiolipin is found almost exclusively in the inner mitochondrial membrane where it is essential for the optimal function of enzymes involved in mitochondrial metabolism.

Cardiolipin is a species of diphosphatidylglycerol lipid comprising two phosphatidylglycerols connected with a glycerol backbone to form a dimeric structure. It has four alkyl groups and potentially carries two negative charges. As there are four distinct alkyl chains in cardiolipin, the molecule has the potential for great complexity. However, in most animal tissues, cardiolipin contains 18-carbon fatty alkyl chains with 2 unsaturated bonds on each of them. It has been proposed that the (18:2) in the four acyl chain configuration is an important structural requirement for the high affinity of cardiolipin to inner membrane proteins in mammalian mitochondria. However, studies with isolated enzyme preparations indicate that its importance may vary depending on the protein examined.

Each of the two phosphates in the molecule can capture one proton. Although it has a symmetric structure, ionization of one phosphate happens at different levels of acidity than ionizing both, with pK1=3 and pK2>7.5. Hence, under normal physiological conditions (a pH of approximately 7.0), the molecule may carry only one negative charge. Hydroxyl groups (—OH and —O—) on the phosphate form stable intramolecular hydrogen bonds, forming a bicyclic resonance structure. This structure traps one proton, which is conducive to oxidative phosphorylation.

During the oxidative phosphorylation process catalyzed by Complex IV, large quantities of protons are transferred from one side of the membrane to another side causing a large pH change. Without wishing to be bound by theory, it has been suggested that cardiolipin functions as a proton trap within the mitochondrial membranes, strictly localizing the proton pool and minimizing pH in the mitochondrial intermembrane space. This function is thought to be due to the unique structure of cardiolipin, which, as described above, can trap a proton within the bicyclic structure while carrying a negative charge. Thus, cardiolipin can serve as an electron buffer pool to release or absorb protons to maintain the pH near the mitochondrial membranes.

In addition, cardiolipin has been shown to play a role in apoptosis. An early event in the apoptosis cascade involves cardiolipin. As discussed in more detail below, a cardiolipin-specific oxygenase produces cardiolipin-hydroperoxides which causes the lipid to undergo a conformational change. The oxidized cardiolipin then translocates from the inner mitochondrial membrane to the outer mitochondrial membrane where it is thought to form a pore through which cytochrome c is released into the cytosol. Cytochrome c can bind to the IP3 receptor stimulating calcium release, which further promotes the release of cytochrome c. When the cytoplasmic calcium concentration reaches a toxic level, the cell dies. In addition, extra-mitochondrial cytochrome c interacts with apoptotic activating factors, causing the formation of apoptosomal complexes and activation of the proteolytic caspase cascade.

Other roles proposed for cardiolipin are: 1) participation in stabilization of the physical properties of the membrane (Schlame et al., 2000; Koshkin and Greenberg, 2002; Ma et al., 2004), for example, membrane fluidity and osmotic stability and 2) participation in protein function via direct interaction with membrane proteins (Schlame et al., 2000; Palsdottir and Hunte, 2004). Cardiolipin has been found in tight association with inner membrane protein complexes such as the cytochrome bcl complex (complex 111). As well, it has been localized to the contact sites of dimeric cytochrome c oxidase, and cardiolipin binding sites have also been found in the ADP/ATP carrier (AAC; for review see Palsdottir and Hunte, 2004). Recent work also suggests a role of cardiolipin in formation of respiratory chain supercomplexes (respirasomes).

The major tetra-acyl molecular species are 18:2 in each of the four fatty acyl positions of the cardiolipin molecule (referred to as the 18:2-18:2-18:2-18:2 cardiolipin species). Remodeling of cardiolipin is essential to obtain this enrichment of cardiolipin with linoleate because cardiolipin synthase has no molecular species substrate specificity for cytidine-5'-diphosphate-1,2-diacyl-sn-glycerol. In addition, the species pattern of cardiolipin precursors is similar enough to imply that the enzymes of the cardiolipin synthetic pathway are not molecular species-selective. Alterations in the molecular composition of cardiolipin are associated with various disease states.

Remodeling of cardiolipin occurs via at least three enzymes. Mitochondrial cardiolipin is remodeled by a deacylation-reacylation cycle in which newly synthesized cardiolipin is rapidly deacylated to monolysocardiolipin (MLCL) and then reacylated back to cardiolipin. MLCL AT1 is responsible for the deacylation and ALCAT1 is responsible for the reacylation. In addition to these mitochondrial and microsomal acyltransferase activities, mitochondrial cardiolipin may be remodeled by a mitochondrial cardiolipin transacylase. Tafazzin (TAZ1) is a cardiolipin transacylase that specifically remodels mitochondrial cardiolipin with linoleic acid.

Regulation of TAZ1

Tafazzin (TAZ1) is a protein that in humans is encoded by the TAZ gene. TAZ1 functions as a phospholipid-lysophospholipid transacylase. TAZ1 is highly expressed in cardiac and skeletal muscle and is involved in the metabolism of cardiolipin.

TAZ1 is involved in the maintenance of the inner membrane of mitochondria. These proteins are involved in maintaining levels of cardiolipin, which is essential for energy production in the mitochondria.

Some mutations in the TAZ gene cause a condition called X-linked dilated cardiomyopathy. This is a condition in which the heart becomes so weakened and enlarged that it cannot pump blood efficiently, leading to heart failure. The decreased heart function can negatively affect many body systems and lead to swelling in the legs and abdomen, fluid in the lungs, and an increased risk of blood clots.

Another mutation in the TAZ gene causes a condition called isolated noncompaction of left ventricular myocardium (INVM). This condition occurs when the lower left chamber of the heart (left ventricle) does not develop correctly. The heart muscle is weakened and cannot pump blood efficiently, often leading to heart failure. Sometimes abnormal heart rhythms (arrhythmias) can also occur.

Barth Syndrome is a heritable disorder of phospholipid metabolism characterized by dilated cardiomyopathy (DCM), skeletal myopathy, neutropenia, growth delay and organic aciduria. The prevalence of Barth Syndrome is estimated at 1/454,000 live births, with an estimated incidence ranging from 1/400,000 to 1/140,000 depending on geographic location. Barth Syndrome is an X-linked disorder, and so disproportionately affects male patients.

Barth Syndrome is caused by mutations in the TAZ gene (tafazzin; Xq28). Defective TAZ1 function results in abnormal remodeling of cardiolipin and compromises mitochondrial structure and respiratory chain function. TAZ1 is expressed at high levels in cardiac and skeletal muscle and is involved in the maintenance of the inner membrane of mitochondria. TAZ1 is involved in maintaining levels of cardiolipin, which is essential for energy production in the mitochondria.

Clinical presentation of Barth Syndrome is highly variable. Most subjects develop DCM during the first decade of life, and typically during the first year of life, which may be accompanied by endocardial fibroelastosis (EFE) and/or left ventricular noncompaction (LVNC). The manifestations of Barth Syndrome may begin in utero, causing cardiac failure, fetal hydrops and miscarriage or stillbirth during the 2nd/3rd trimester of pregnancy. Ventricular arrhythmia, especially during adolescence, can lead to sudden cardiac death. There is a significant risk of stroke. Skeletal (mostly proximal) myopathy causes delayed motor milestones, hypotonia, severe lethargy or exercise intolerance. Here is a tendency to hypoglycemia during the neonatal period. Ninety percent of patients show mild to severe intermittent or persistent neutropenia with a risk of septicemia, severe bacterial sepsis, mouth ulcers and painful gums. Lactic acidosis and mild anemia may occur. Affected boys usually show delayed puberty and growth delay that is observed until the late teens or early twenties, when a substantial growth spurt often occurs. Patients may also present severe difficulties with adequate food intake. Episodic diarrhea is common. Many patients have a similar facial appearance with chubby cheeks, deep-set eyes and prominent ears.

In some embodiments, treatment with an aromatic-cationic peptide, such as, e.g., D-Arg-2'6'-Dmt-Lys-Phe-NH$_2$, increases the expression of TAZ1 in the myocardium in mammalian subjects that have suffered or are at risk of suffering heart failure.

In some embodiments, TAZ1 expression level is increased by about 0.25 fold to about 0.5 fold, or about 0.5 fold to about 0.75 fold, or about 0.75 fold to about 1.0 fold, or about 1.0 fold to about 1.5 fold.

Regulation of MLCL AT1

Monolysocardiolipin acyltransferase (MLCL AT1) catalyzes the acylation of MLCL to cardiolipin in mammalian tissues.

In some embodiments, treatment with an aromatic-cationic peptide, such as, e.g., D-Arg-2'6'-Dmt-Lys-Phe-NH$_2$, decreases the expression of MLCL AT1 in the myocardium in mammalian subjects that have suffered or are at risk of suffering heart failure.

In some embodiments, reducing MLCL AT1 expression level is a reduction measured by about 1 fold to about 1.5 fold reduction, or about 1.5 fold to about 2.0 fold reduction, or about 2.0 fold to about 2.5 fold reduction, or about 2.5 fold to about 3.0 fold reduction.

ALCAT1

Acyl-CoA lysocardiolipin acyltransferase 1 (ALCAT1) was initially identified as a microsomal lysocardiolipin acyltransferase. ALCAT1 possesses acyltransferase activities toward lysophosphatidylinositol (LPI) and lysophosphatidylglycerol (LPG).

ALCAT1 recognizes both monolysocardiolipin and dilysocardiolipin as substrates with a preference for linoleoyl-CoA and oleoyl-CoA as acyl donors. ALCAT1 acts as a remodeling enzyme for cardiolipin.

In some embodiments, treatment with an aromatic-cationic peptide, such as, e.g., D-Arg-2'6'-Dmt-Lys-Phe-NH$_2$, decreases the expression of ALCAT1 in the myocardium in mammalian subjects that have suffered or are at risk of suffering heart failure.

In some embodiments, reducing ALCAT1 expression level is a reduction measured by about 1 fold to about 1.5 fold reduction, or about 1.5 fold to about 2.0 fold reduction, or about 2.0 fold to about 2.5 fold reduction, or about 2.5 fold to about 3.0 fold reduction.

Therapeutic Methods

The following discussion is presented by way of example only, and is not intended to limit the disclosed methods and compositions to a specific disease or disease state. It is understood that lowering the expression of MLCL AT1 or ALCAT1 and/or raising the expression TAZ1 in a subject in need thereof will reduce the risk of any number of negative cardiac, stenotic or vascular events. One aspect of the present technology includes methods of treating heart failure in a subject having or suspected of having an elevated MLCL AT1 or ALCAT1 expression and/or lowered TAZ1 expression for therapeutic purposes. In therapeutic applications, compositions or medicaments comprising an aromatic-cationic peptide such as D-Arg-2'6'-Dmt-Lys-Phe-NH$_2$ or a pharmaceutically acceptable salt thereof, such as acetate or trifluoroacetate salt, are administered to a subject suspected of, or already suffering from such a disease in an amount sufficient to cure, or at least partially arrest, the symptoms of the disease, including its complications and intermediate pathological phenotypes in development of the disease. As such, in some embodiments, the present technology provides methods of treating an individual having or suspected of having an elevated MLCL AT1 or ALCAT1 expression level afflicted with heart failure. Alternatively, or additionally, in some embodiments, the present technology provides methods of treating an individual having or suspected of having an decreased TAZ1 expression afflicted with heart failure.

Methods of Detection and Diagnosis

The present disclosure provides methods for diagnosis of diseases and conditions characterized by aberrant cardiolipin isoform expression, and/or aberrant cardiolipin remodeling gene sequences or gene expression levels. For example, the present disclosure provides methods for diagnosis of heart failure, monitoring the treatment of heart failure, assessing mitochondrial dysfunction, detecting mutant nucleic acid sequences, detecting levels of nucleic acid sequences, and assessing cardiolipin content and composition. For example, in some embodiments, the methods comprise detecting the nucleic acid sequence (DNA or RNA) and/or levels of cardiolipin remodeling enzyme RNAs and/or cardiolipin isoforms in a biological sample from the subject. By way of example, but not by way of limitation, subjects presenting with heart failure display aberrant levels of TAZ1, MLCL AT1 or ALCAT1 mRNAs and levels of the 18:2 cardiolipin isoform compared to normal control subjects. In another non-limiting example, subjects suffering from or at risk of, e.g., Barth syndrome may exhibit aberrant cardiolipin isoform expression, and/or aberrant cardiolipin remodeling genes (e.g., gene mutations) or aberrant cardiolipin remodeling gene expression levels. The methods disclosed herein are directed to detecting such abnormalities, thereby allowing for diagnosis, and appropriate therapeutic administration or modification.

Levels of TAZ1, MLCL AT1 or ALCAT1 mRNAs may be measured (e.g., in a biological sample from a subject) by any suitable method known in the art, including, but not limited to, e.g., RT-PCR, in situ hybridization, or Northern blotting. Such methods are well known in the art.

By way of example but not by way of limitation, where the level of TAZ1, MLCL AT1 or ALCAT1 nucleic acid is measured, the step of measuring the level of nucleic acid comprises the steps of (a) contacting a biological sample with an oligonucleotide probe or oligonucleotide primer specific for TAZ1, MLCL AT1 or ALCAT1 nucleic acid and (b) detecting the level of TAZ1, MLCL AT1 or ALCAT1 nucleic acid present in the sample by observing the level of interaction between said oligonucleotide probe or oligonucleotide primer and the TAZ1, MLCL AT1 or ALCAT1 nucleic acid. Such probes and primers predominantly, preferably specifically, bind to TAZ1, MLCL AT1 or ALCAT1 nucleic acid in a manner sufficient to enable detection by known methods. The "level of interaction," for example the level of binding of a probe or the level of amplification brought about by a primer (e.g., in the context of an amplification reaction), provides an indication of the level or amount of nucleic acid (for example, cDNA or RNA) present in the sample and thus the level or amount of the TAZ1, MLCL AT1 or ALCAT1. Such observations may be carried out using known methodologies and protocols. For example, where an oligonucleotide probe is used to detect the level of TAZ1, MLCL AT1 or ALCAT1 nucleic acid, for example mRNA, Northern hybridizations, dot-blot, and in situ hybridizations can be used. Where an oligonucleotide primer is used to detect TAZ1, MLCL AT1 or ALCAT1 nucleic acid, primer extension reactions, such as the polymerase chain reaction (PCR), for example quantitative PCR, can be carried out upon cDNA or RNA samples, to determine the level of TAZ1, MLCL AT1 or ALCAT1 nucleic acid.

Other techniques for amplification include, for example, nucleic acid sequence based amplification (NASBA, e.g., Guatelli, et al., Proc. Nat'l. Acad. Sci. 87, 1874 (1990), incorporated herein by reference), strand displacement amplification (SDA, e.g., Walker, et al., Proc. Nat'l. Acad.

Sci. 89, 392-96 (1992), incorporated herein by reference), ligase chain reaction (LCR, e.g., Kalin, et al., Mutat. Res., 283, 119-23 (1992), incorporated herein by reference), transcription mediated amplification (TMA, e.g., La Rocco, et al., Eur. J. Clin. Microbiol. Infect. Dis., 13, 726-31 (1994), incorporated herein by reference), and rolling circle amplification (RCA, e.g., Lizardi, et al., Nat. Genet., 19, 225-32 (1998), incorporated herein by reference).

In some embodiments, a transcriptomic evaluation of the nucleic acid levels of TAZ1, MLCL AT1 or ALCAT1 is performed. In some embodiments, the transcriptome is the set of all RNA molecules, including mRNA, rRNA, tRNA, and other non-coding RNA produced in one or a population of cells or tissues from the subject. In some embodiments, the transcriptome includes only mRNA molecules in one or a population of cells or tissues from the subject.

The content and composition of mitochondrial cardiolipin and/or the presence and amount of TAZ1, MLCL AT1 or ALCAT1 protein may be measured using any suitable method known in the art, including, but not limited to, e.g., chromatography, mass spectrometry, ELISA, Western blotting, immunodetection, or immunoprecipitation. As used herein, "content and composition" of cardiolipin refers to the cardiolipin isoforms present in a subject, such as, for example, the presence of a particular cardiolipin isoform or the ratio of particular cardiolipin isoforms. By way of example, but not by way of limitation, cardiolipin, TAZ1, MLCL AT1 or ALCAT1 levels are determined, and cardiolipin isoforms detectect using antibodies.

For example, antibodies, or fragments of antibodies, specific for a cardiolipin isoform or protein of interest can be used to quantitatively or qualitatively detect the presence of the isoform or protein. This can be accomplished, for example, by immunofluorescence techniques. Antibodies (or fragments thereof) can, additionally, be employed histologically, as in immunofluorescence or immunoelectron microscopy, for in situ detection of an isoform or protein of interest. In situ detection can be accomplished by removing a histological specimen (e.g., a biopsy specimen) from a patient, and applying thereto a labeled antibody thereto that is directed to an isoform or a protein. The antibody (or fragment) is preferably applied by overlaying the labeled antibody (or fragment) onto a biological sample. Through the use of such a procedure, it is possible to determine not only the presence of the protein or isoform of interest, but also its distribution, its presence in cells (e.g., brain cells, heart cells, lymphocytes, etc.) within the sample. A wide variety of well-known histological methods (such as staining procedures) can be utilized in order to achieve such in situ detection.

Immunoassays for a protein or isoform of interest typically comprise incubating a biological sample of a detectably labeled antibody capable of identifying a protein or isoform of interest, and detecting the bound antibody by any of a number of techniques well-known in the art. The term "labeled" can refer to direct labeling of the antibody via, e.g., coupling (i.e., physically linking) a detectable substance to the antibody, and can also refer to indirect labeling of the antibody by reactivity with another reagent that is directly labeled. Examples of indirect labeling include detection of a primary antibody using a fluorescently labeled secondary antibody.

For example, the biological sample can be brought in contact with and immobilized onto a solid phase support or carrier such as nitrocellulose, or other support which is capable of immobilizing cells, cell particles or soluble proteins. The support can then be washed with suitable buffers followed by treatment with the detectably labeled specific antibody. The solid phase support can then be washed with the buffer a second time to remove unbound antibody. The amount of bound label on support can then be detected by conventional means.

By "solid phase support or carrier" in the context of proteinaceous or cardiolipin isoform agents is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. In some embodiments, supports include polystyrene beads. Those skilled in the art will know many other suitable carriers for binding antibody or antigen, or will be able to ascertain the same by use of routine experimentation.

One of the ways in which a specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville, Md.); Voller, A. et al., 1978, J. Clin. Pathol. 31:507-520; Butler, J. E., 1981, Meth. Enzymol. 73:482-523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a protein of interest through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). Radioactive isotopes (e.g., $^{125}I$, $^{131}I$, $^{35}S$ or $^3H$) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. By way of example but not by way of limitation, among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylene diaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present technology. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Antibodies of the present technology may be a monoclonal antibody or a polyclonal antibody. Methods for deriving monoclonal and polyclonal antibodies are well known in the art. For the production of both monoclonal and polyclonal antibodies, the experimental animal is a suitable mammal such as, but not restricted to, a goat, rabbit, rat or mouse. In one embodiment, an antibody of the invention is a monoclonal antibody.

Monoclonal antibodies are immunoglobulin molecules that are identical to each other and have a single binding specificity and affinity for a particular epitope. Monoclonal antibodies (mAbs) of the present technology can be produced by a variety of techniques, including conventional monoclonal antibody methodology e.g., the standard somatic cell hybridization technique of Kohler and Milstein (1975) Nature 256: 495, or viral or oncogenic transformation of B lymphocytes. In some embodiments, the animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

To generate hybridomas that produce monoclonal antibodies of the present technology, splenocytes and/or lymph node cells from immunized mice can be isolated and fused to an appropriate immortalized cell line, such as a mouse myeloma cell line. The resulting hybridomas can be screened for the production of antigen-specific antibodies. The antibody secreting hybridomas can be re-plated, screened again, and if still positive for suitable IgG, the hybridomas can be subcloned at least twice by limiting dilution. The stable subclones can then be cultured in vitro to generate small amounts of antibody in tissue culture medium for characterization.

An antibody of the present technology may be prepared, expressed, created or isolated by recombinant means, such as (a) antibodies isolated from an animal (e.g., a mouse) that is transgenic or transchromosomal for the immunoglobulin genes of interest or a hybridoma prepared therefrom, (b) antibodies isolated from a host cell transformed to express the antibody of interest, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

In some embodiments, a proteomic evaluation of the levels of TAZ1, MLCL AT1 or ALCAT1 protein is performed. In some embodiments, the proteome is the set of all protein molecules produced in one or a population of cells or tissues from the subject.

In some embodiments, levels of cardiolipin and/or cardiolipin isoforms are determined for one or a population of cells or tissues from the subject.

For purposes of diagnosing heart failure, assessing mitochondrial dysfunction, and assessing cardiolipin content and composition, a subject's biological sample may be compared to a sample from a normal control subject. For purposes of monitoring treatment for heart failure, a subject's biological sample may be compared to a sample from a normal control subject and/or to a sample previously collected from the subject, such as prior to the start of treatment or at an earlier time point in the course of treatment.

According to the methods, the subject's biological sample may be any sample that provides a suitable amount of RNA or mitochondrial cardiolipin to perform the necessary detection method. Biological samples suitable for the disclosed methods include but are not limited to a tissue, a cell, or a mitochondria from the subject. In some embodiments, the sample comprises a tissue. In some embodiments, the tissue comprises a cardiac tissue. In some embodiments, the tissue comprises a non-cardiac tissue. In some embodiments, the sample comprises a cell. In some embodiments, the cell is a blood cell. In some embodiments, the blood cell is a peripheral blood mononuclear cell (PBMC) or a leukocyte. In some embodiments, the sample comprises mitochondria isolated from cardiac tissue or non-cardiac tissue.

In some embodiments, the methods further comprise administering to the subject a therapeutically effective amount of the peptide D-Arg-2'6'-Dmt-Lys-Phe-NH$_2$ or a pharmaceutically acceptable salt thereof. In some embodiments, the methods further comprise administering to the subject a cardiovascular agent. In some embodiments, the cardiovascular agent is selected from the group consisting of: an anti-arrhythmia agent, a vasodilator, an anti-anginal agent, a corticosteroid, a cardioglycoside, a diuretic, a sedative, an angiotensin converting enzyme (ACE) inhibitor, an angiotensin II antagonist, a thrombolytic agent, a calcium channel blocker, a throboxane receptor antagonist, a radical scavenger, an anti-platelet drug, a β-adrenaline receptor blocking drug, α-receptor blocking drug, a sympathetic nerve inhibitor, a digitalis formulation, an inotrope, and an antihyperlipidemic drug.

Prophylactic Methods

In one aspect, the present technology provides a method for preventing heart failure in a subject having or suspected of having one or more of an elevated MLCL AT1 or ALCAT1 expression and/or decreased TAZ1 expression, by administering to the subject an compositions or medicaments comprising an aromatic-cationic peptide such as D-Arg-2'6'-Dmt-Lys-Phe-NH$_2$ or a pharmaceutically acceptable salt thereof, such as acetate or trifluoroacetate salt, that normalizes one or more of the MLCL AT1, ALCAT1, or TAZ1 expression levels. Subjects at risk for heart failure can be identified by, e.g., any or a combination of diagnostic or prognostic assays as described herein. In prophylactic applications, pharmaceutical compositions or medicaments of aromatic-cationic peptides are administered to a subject susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. Administration of a prophylactic aromatic-cationic can occur prior to the manifestation of symptoms characteristic of the disease or disorder, such that the disease or disorder is prevented or, alternatively, delayed in its progression. The appropriate compound can be determined based on screening assays described above.

Subjects diagnosed with or at risk for heart failure may exhibit one or more of the following non-limiting risk factors: high blood pressure; coronary artery disease; heart attack; irregular heartbeats; diabetes; some diabetes medications (e.g., rosiglitazone and pioglitazone have been found to increase the risk of heart failure); sleep apnea; congenital heart defects; viral infection; alcohol use; obesity, lifestyle (e.g., smoking, sedentary lifestyle), high cholesterol, family history, stress, and kidney conditions.

Determination of the Biological Effect of the Aromatic-Cationic Peptide-Based Therapeutic In various embodiments, suitable in vitro or in vivo assays are performed to determine the effect of a specific aromatic-cationic peptide-based therapeutic and whether its administration is indicated for treatment. In various embodiments, in vitro assays can be performed with representative animal models, to determine if a given aromatic-cationic peptide-based therapeutic exerts the desired effect in reducing MLCL AT1 and ALCAT 1 expression, increasing TAZ1 expression, and preventing or treating heart failure. Compounds for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

HF has been induced in different species with volume overload, pressure overload, fast pacing, myocardial ischemia, cardiotoxic drugs, or genetically modified models. Models using pressure overload have been most commonly used. Hypertension is associated with an increased risk for the development of HF. In one mouse model, angiotensin II (Ang II) increases blood pressure and induces cardiomyocyte hypertrophy, increased cardiac fibrosis, and impaired cardiomyocyte relaxation. Infusion of angiotensin to mice by mini osmotic pump increases systolic and diastolic blood pressure, increases heart weight and left ventricular thickness (LVMI), and impaired myocardial performance index (MPI). MLCL AT1, ALCAT1, and TAZ1 expression levels are monitored at various time points before, during and after HF induction.

In a second illustrative mouse model, sustained high level expression of Gaq can lead to marked myocyte apoptosis, resulting in cardiac hypertrophy and heart failure by 16 weeks of age (D'Angelo et al., 1998). The β-adrenergic receptors (βARs) are primarily coupled to the heterotrimeric G protein, Gs, to stimulate adenylyl cyclase activity. This association generates intracellular cAMP and protein kinase A activation, which regulate cardiac contractility and heart rate. Overexpression of Gaq leads to decreased responsiveness to β-adrenergic agonists and results in HF. MLCL AT1, ALCAT1, and TAZ1 expression levels are monitored at various time points before, during and after HF induction.

Experimental constriction of the aorta by surgical ligation is also widely used as a model of HF. Transaortic constriction (TAC) results in pressure overload induced HF, with increase in left ventricular (LV) mass. TAC is performed as described by Tamayski O et al. (2004) using a 7-0 silk double-knot suture to constrict the ascending aorta. After TAC, mice develop HF within a period of 4 weeks. MLCL AT1, ALCAT1, and TAZ1 expression levels are monitored at various timepoints before, during and after HF induction.

Modes of Administration and Effective Dosages

Any method known to those in the art for contacting a cell, organ or tissue with a peptide may be employed. Suitable methods include in vitro, ex vivo, or in vivo methods. In vivo methods typically include the administration of an aromatic-cationic peptide, such as those described above, to a mammal, suitably a human. When used in vivo for therapy, the aromatic-cationic peptides are administered to the subject in effective amounts (i.e., amounts that have desired therapeutic effect). The dose and dosage regimen will depend upon the degree of the infection in the subject, the characteristics of the particular aromatic-cationic peptide used, e.g., its therapeutic index, the subject, and the subject's history.

The effective amount may be determined during pre-clinical trials and clinical trials by methods familiar to physicians and clinicians. An effective amount of a peptide useful in the methods may be administered to a mammal in need thereof by any of a number of well-known methods for administering pharmaceutical compounds. The peptide may be administered systemically or locally.

The peptide may be formulated as a pharmaceutically acceptable salt. The term "pharmaceutically acceptable salt" means a salt prepared from a base or an acid which is acceptable for administration to a patient, such as a mammal (e.g., salts having acceptable mammalian safety for a given dosage regime). However, it is understood that the salts are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a peptide contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucuronic, mandelic, mucic, nicotinic, orotic, pamoic, pantothenic, sulfonic acids (e.g., benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like. In some embodiments, the salt is an acetate or trifluoroacetate salt.

The aromatic-cationic peptides described herein can be incorporated into pharmaceutical compositions for administration, singly or in combination, to a subject for the treatment or prevention of a disorder described herein. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral (e.g., intravenous, intradermal, intraperitoneal or subcutaneous), oral, inhalation, transdermal (topical), intraocular, iontophoretic, and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of drug, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, a composition for parenteral administration must be sterile and should be fluid to the extent that easy syringability exists. It should be stable under the conditions of manufacture and storage and must be preserved against the contaminating action of microorganisms such as bacteria and fungi.

The aromatic-cationic peptide compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressurized container or dispenser, which contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays. For transdermal administration, the active compounds are formulated into ointments, salves, gels, or creams as generally known in the art. In one embodiment, transdermal administration may be performed my iontophoresis.

A therapeutic protein or peptide can be formulated in a carrier system. The carrier can be a colloidal system. The colloidal system can be a liposome, a phospholipid bilayer vehicle. In one embodiment, the therapeutic peptide is encapsulated in a liposome while maintaining peptide integrity. s one skilled in the art would appreciate, there are a variety of methods to prepare liposomes. (See Lichtenberg et al., *Methods Biochem. Anal.*, 33:337-462 (1988); Anselem et al., *Liposome Technology*, CRC Press (1993)). Liposomal formulations can delay clearance and increase cellular uptake (See Reddy, *Ann. Pharmacother.*, 34(7-8):915-923 (2000)). An active agent can also be loaded into a particle prepared from pharmaceutically acceptable ingredients including, but not limited to, soluble, insoluble, permeable, impermeable, biodegradable or gastroretentive polymers or liposomes. Such particles include, but are not limited to, nanoparticles, biodegradable nanoparticles, microparticles, biodegradable microparticles, nanospheres, biodegradable nanospheres, microspheres, biodegradable microspheres, capsules, emulsions, liposomes, micelles and viral vector systems.

The carrier can also be a polymer, e.g., a biodegradable, biocompatible polymer matrix. In one embodiment, the therapeutic peptide can be embedded in the polymer matrix, while maintaining protein integrity. The polymer may be natural, such as polypeptides, proteins or polysaccharides, or synthetic, such as poly α-hydroxy acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, *Ann. Pharmacother.*, 34(7-8):915-923 (2000)). A polymer formulation for human growth hormone (hGH) has been used in clinical trials. (See Kozarich and Rich, *Chemical Biology*, 2:548-552 (1998)).

Examples of polymer microsphere sustained release formulations are described in PCT publication WO 99/15154 (Tracy et al.), U.S. Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using known techniques. The materials can also be obtained commercially, e.g., from Alza Corporation and Nova Pharmaceuticals, Inc. Liposomal suspensions (including liposomes targeted to specific cells with monoclonal antibodies to cell-specific antigens) can also be used as pharmaceutically acceptable carriers. These can be prepared according to methods known to those skilled in the art, for example, as described in U.S. Pat. No. 4,522,811.

The therapeutic compounds can also be formulated to enhance intracellular delivery. For example, liposomal delivery systems are known in the art, see, e.g., Chonn and Cullis, "Recent Advances in Liposome Drug Delivery Systems," *Current Opinion in Biotechnology* 6:698-708 (1995); Weiner, "Liposomes for Protein Delivery: Selecting Manufacture and Development Processes," *Immunomethods*, 4(3): 201-9 (1994); and Gregoriadis, "Engineering Liposomes for Drug Delivery: Progress and Problems," *Trends Biotechnol.*, 13(12):527-37 (1995). Mizguchi et al., *Cancer Lett.*, 100: 63-69 (1996), describes the use of fusogenic liposomes to deliver a protein to cells both in vivo and in vitro.

Dosage, toxicity and therapeutic efficacy of the therapeutic agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to determine useful doses in humans accurately. Levels in plasma may be measured, for example, by high performance liquid chromatography.

Typically, an effective amount of the aromatic-cationic peptides, sufficient for achieving a therapeutic or prophylactic effect, range from about 0.000001 mg per kilogram body weight per day to about 10,000 mg per kilogram body weight per day. Suitably, the dosage ranges are from about 0.0001 mg per kilogram body weight per day to about 100 mg per kilogram body weight per day. For example dosages can be 1 mg/kg body weight or 10 mg/kg body weight every day, every two days or every three days or within the range of 1-10 mg/kg every week, every two weeks or every three weeks. In one embodiment, a single dosage of peptide ranges from 0.001-10,000 micrograms per kg body weight. In one embodiment, aromatic-cationic peptide concentrations in a carrier range from 0.2 to 2000 micrograms per delivered milliliter. An exemplary treatment regime entails administration once per day or once a week. In therapeutic applications, a relatively high dosage at relatively short intervals is sometimes required until progression of the disease is reduced or terminated, and preferably until the subject shows partial or complete amelioration of symptoms of disease. Thereafter, the patient can be administered a prophylactic regime.

In some embodiments, a therapeutically effective amount of an aromatic-cationic peptide may be defined as a concentration of peptide at the target tissue of $10^{-12}$ to $10^{-6}$ molar, e.g., approximately $10^{-7}$ molar. This concentration may be delivered by systemic doses of 0.001 to 100 mg/kg or equivalent dose by body surface area. The schedule of doses would be optimized to maintain the therapeutic concentration at the target tissue, most preferably by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

The mammal treated in accordance present methods can be any mammal, including, for example, farm animals, such as sheep, pigs, cows, and horses; pet animals, such as dogs and cats; laboratory animals, such as rats, mice and rabbits. In a preferred embodiment, the mammal is a human.

Combination Therapy with an Aromatic-Cationic Peptide and Other Therapeutic Agents In some embodiments, the aromatic-cationic peptides may be combined with one or more additional agents for the prevention or treatment of heart failure. Drug treatment for heart failure typically involves diuretics, ACE inhibitors, digoxin (also called digitalis), calcium channel blockers, and beta-blockers. In mild cases, thiazide diuretics, such as hydrochlorothiazide at 25-50 mg/day or chlorothiazide at 250-500 mg/day, are useful. However, supplemental potassium chloride may be needed, since chronic diuresis causes hypokalemis alkalosis. Moreover, thiazide diuretics usually are not effective in patients with advanced symptoms of heart failure. Typical doses of ACE inhibitors include captopril at 25-50 mg/day and quinapril at 10 mg/day.

In one embodiment, the aromatic-cationic peptide is combined with an adrenergic beta-2 agonist. An "adrenergic beta-2 agonist" refers to adrenergic beta-2 agonists and analogues and derivatives thereof, including, for example, natural or synthetic functional variants, which have adrenergic beta-2 agonist biological activity, as well as fragments of an adrenergic beta-2 agonist having adrenergic beta-2 agonist biological activity. The term "adrenergic beta-2 agonist biological activity" refers to activity that mimics the effects of adrenaline and noradrenaline in a subject and which improves myocardial contractility in a patient having heart failure. Commonly known adrenergic beta-2 agonists include, but are not limited to, clenbuterol, albuterol, formeoterol, levalbuterol, metaproterenol, pirbuterol, salmeterol, and terbutaline.

In one embodiment, the aromatic-cationic peptide is combined with an adrenergic beta-1 antagonist. Adrenergic beta-1 antagonists and adrenergic beta-1 blockers refer to adrenergic beta-1 antagonists and analogues and derivatives thereof, including, for example, natural or synthetic functional variants which have adrenergic beta-1 antagonist biological activity, as well as fragments of an adrenergic beta-1 antagonist having adrenergic beta-1 antagonist biological activity. Adrenergic beta-1 antagonist biological activity refers to activity that blocks the effects of adrenaline on beta receptors. Commonly known adrenergic beta-1 antagonists include, but are not limited to, acebutolol, atenolol, betaxolol, bisoprolol, esmolol, and metoprolol.

Clenbuterol, for example, is available under numerous brand names including Spiropent® (Boehinger Ingelheim), Broncodil® (Von Boch I), Broncoterol® (Quimedical PT), Cesbron® (Fidelis PT), and Clenbuter® (Biomedica Foscama). Similarly, methods of preparing adrenergic beta-1 antagonists such as metoprolol and their analogues and derivatives are well-known in the art. Metoprolol, in particular, is commercially available under the brand names Lopressor® (metoprolol tartate) manufactured by Novartis Pharmaceuticals Corporation, One Health Plaza, East Hanover, N.J. 07936-1080. Generic versions of Lopressor® are also available from Mylan Laboratories Inc., 1500 Corporate Drive, Suite 400, Canonsburg, Pa. 15317; and Watson Pharmaceuticals, Inc., 360 Mt. Kemble Ave. Morristown, N.J. 07962. Metoprolol is also commercially available under the brand name Toprol XL®, manufactured by Astra Zeneca, LP.

In one embodiment, an additional therapeutic agent is administered to a subject in combination with an aromatic cationic peptide, such that a synergistic therapeutic effect is produced. Therefore, lower doses of one or both of the therapeutic agents may be used in treating heart failure, resulting in increased therapeutic efficacy and decreased side-effects.

In any case, the multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

EXAMPLES

The present invention is further illustrated by the following examples, which should not be construed as limiting in any way.

Example 1—Effects of Aromatic-Cationic Peptides on Heart Mitochondrial Cardiolipin in a Dog Model of Heart Failure In this Example, the effect of aromatic-cationic peptide such as D-Arg-2'6'-Dmt-Lys-Phe-NH$_2$ on heart mitochondrial cardiolipin levels in dogs with coronary microembolization-induced heart failure will be investigated.

Methods

Heart failure will be induced in dogs via multiple sequential intracoronary microembolizations as described in Sabbah, et al., *Am J Physiol.* (1991) 260:H1379-84, herein incorporated by reference in its entirety. Half the dogs will be subsequently treated with the mitochondrial peptide; the other half will be treated with drug vehicle and serve as controls. Peptide treatment will be started upon induction of heart failure (HF), defined as left ventricular ejection fraction of approximately 30%. The daily dose of the peptide will be 0.5 mg/kg/day administered intravenously. At the end of the treatment phase (12 weeks) dogs in both the vehicle and treatment groups will be sacrificed and a sample of heart muscle from the left ventricle will be removed, washed with saline, and immediately frozen and stored at −80° C. For cardiolipin analysis, lipids will be extracted from the heart tissue sample with a chloroform/methanol solution (Bligh Dyer extraction). Individual lipid extracts will be reconstituted with chloroform:methanol (1:1), flushed with N$_2$, and then stored at −20° C. before analysis via electrospray ionization mass spectroscopy using a triple-quadrupole mass spectrometer equipped with an automated nanospray apparatus. Enhanced multidimensional mass spectrometry-based shotgun lipidomics for cardiolipin will be performed as described by Han, et al., "*Shotgun lipid-* omics of cardiolipin molecular species in lipid extracts of biological samples," *J Lipid Res* 47(4)864-879 (2006).

Anticipated Results

It is anticipated that the 18:2 cardiolipin species will be reduced in untreated HF dogs (HF-CON) (p<0.05) as compared to normal cardiac tissue from normal dogs (NL). FIG. 1. However, it is anticipated that HF dogs treated with D-Arg-2'6'-Dmt-Lys-Phe-NH$_2$ (HF-AP) will have levels of 18:2 cardiolipin similar to the NL dogs and greater than HF-CON.

It is anticipated that the 18:2 cardiolipin species will be reduced in HF. It is anticipated that the reduction of 18:2 cardiolipin will lead to poor oxidative phosphorylation and subsequent LV dysfunction. Chronic treatment with D-Arg-2'6'-Dmt-Lys-Phe-NH$_2$ is anticipated to normalize 18:2 cardiolipin, which will lead to improved LV function and rate of mitochondrial ATP synthesis.

These results are anticipated to show that aromatic-cationic peptides of the present disclosure, such as D-Arg-2'6'-Dmt-Lys-Phe-NH$_2$, or a pharmaceutically acceptable salt thereof, such as acetate or trifluoroacetate salt, are useful in the prevention and treatment of diseases and conditions associated with aberrant cardiolipin levels. In particular, these results will show that aromatic-cationic peptides of the present disclosure, such as D-Arg-2'6'-Dmt-Lys-Phe-NH$_2$, or a pharmaceutically acceptable salt thereof, such as acetate or trifluoroacetate salt, are useful in methods comprising administration of the peptide to subjects in need of normalization of cardiolipin levels and remodeling.

Example 2—Effects of Aromatic-Cationic Peptides on MLCL AT1, ALCAT1, and TAZ1 Expression in a Dog Model of Heart Failure In this Example, the effect of the aromatic-cationic peptide D-Arg-2'6'-Dmt-Lys-Phe-NH$_2$ on cardiolipin remodeling enzymes, MLCL AT1, ALCAT1, and TAZ1 in dogs with coronary microembolization-induced heart failure will be investigated.

Methods

Heart failure will be induced in dogs via multiple sequential intracoronary microembolizations as described in Sabbah, et al., *Am J Physiol*. (1991) 260:H1379-84, herein incorporated by reference in its entirety.

Twelve dogs will be subject to coronary microembolization-induced heart failure (LV ejection fraction ~30%). Subjects will be randomized into D-Arg-2'6'-Dmt-Lys-Phe-NH$_2$-treated and control groups for a three-month trial. Subjects will receive subcutaneous injections of D-Arg-2'6'-Dmt-Lys-Phe-NH$_2$ (0.5 mg/kg once daily, n=6) or saline (Untreated-HF Control, n=6). RNA will be prepared from LV tissue of all subjects at the end of the treatment phase and from the LV of six normal subject controls. Levels of TAZ1 mRNA will be determined by real-time PCR. Changes in mRNA levels will be expressed as fold reduction using the CT Method, with normalization to a glyceraldehyde 1,3 diphosphate dehydrogenase (GAPDH) internal control.

Results

Compared to normal level (NL), it is anticipated that mRNA levels of TAZ1 in untreated HF dogs will decrease (e.g., about 2 to about 2.25-fold or more) while mRNA of MLCLAT1 and ALCAT1 will increase (e.g., about 2 to about 2.60-fold or more and about 3 to about 3.56-fold or more, respectively). It is anticipated that treatment with D-Arg-2'6'-Dmt-Lys-Phe-NH$_2$ will attenuate the decrease of TAZ1 (e.g., by about 1-1.23 fold or more) and will reduce the increase in MLCLAT1 and ALCAT1 (e.g., by about 1 to about 1.18-fold or more and by about 1 to about 1.54-fold or more, respectively).

HF is associated with dysregulation of cardiolipin remodeling enzymes that can lead to pathologic remodeling of cardiolipin and to structural and functional mitochondrial abnormalities. It is anticipated that chronic therapy with D-Arg-2'6'-Dmt-Lys-Phe-NH$_2$ will partially reverse these maladaptations thus allowing for resumption of physiologic post-biosynthesis remodeling of cardiolipin.

These results are anticipated to show that aromatic-cationic peptides of the present disclosure, such as D-Arg-2'6'-Dmt-Lys-Phe-NH$_2$, or a pharmaceutically acceptable salt thereof, such as acetate or trifluoroacetate salt, are useful in the prevention and treatment of diseases and conditions associated with reduced TAZ1 expression levels. In particular, these results are anticipated to show that aromatic-cationic peptides of the present disclosure, such as D-Arg-2'6'-Dmt-Lys-Phe-NH$_2$, or a pharmaceutically acceptable salt thereof, such as acetate or trifluoroacetate salt, are useful in methods comprising administration of the peptide to subjects in need of normalization of TAZ1 expression levels, such as, for example, subjects having Barth Syndrome.

Example 3: Diagnosis of Heart Failure

This example will demonstrate methods of the present technology for the diagnosis of heart failure in a subject in need thereof. In particular, the example will demonstrate the detection of TAZ1, MLCL AT1, or ALCAT1 mRNA and cardiolipin content and composition in a biological sample from the subject for the diagnosis of heart failure.

Methods

For cardiolipin measurements, lipids are extracted from cellular samples from the subject, such as including, but not limited to, cardiac tissue, non-cardiac tissue, peripheral blood cells, such as peripheral blood mononuclear cells (PBMCs) and leukocytes, and isolated mitochondria. Lipids are extracted from the sample with a chloroform/methanol solution (Bligh Dyer extraction). Individual lipid extracts are reconstituted with chloroform:methanol (1:1), flushed with N$_2$, and stored at −20° C. for analysis via electrospray ionization mass spectroscopy using a triple-quadrupole mass spectrometer equipped with an automated nanospray apparatus. Enhanced multidimensional mass spectrometry-based shotgun lipidomics for cardiolipin is performed as described by Han, et al., *Shotgun lipidomics of cardiolipin molecular species in lipid extracts of biological samples*," *J Lipid Res* 47(4)864-879 (2006). Illustrative results for this analysis are shown in Example 1 above.

For mRNA measurements, RNA is prepared from cellular samples from the subject, such as including, but not limited to, cardiac tissue, non-cardiac tissue, peripheral blood cells, such as peripheral blood mononuclear cells (PBMCs) and leukocytes, and isolated mitochondria. Levels of mRNAs are measured using methods known in the art, such as those exemplified in Example 2 above.

Results

It is expected that individuals with heart failure will display aberrant levels of one or more of TAZ1, MLCL AT1, and ALCAT1 mRNAs compared to a normal control subject. TAZ1 mRNAs are expected to be reduced compared to the control, while MLCL AT1, and ALCAT1 mRNAs are expected to be elevated. It is further expected that subjects with heart failure will display aberrant cardiolipin remodeling compared to a normal control subject, with reduced levels of the 18:2 cardiolipin species compared to a control.

These results will show that the methods of the present technology are useful for detecting the levels of TAZ1, MLCL AT1, and ALCAT1 mRNA and cardiolipin content and composition for the diagnosis of heart failure in a subject in need thereof.

Example 4: Monitoring Treatment for Heart Failure

This example will demonstrate methods of the present technology for monitoring of treatment for heart failure in a subject in need thereof. In particular, the example will demonstrate the detection of TAZ1, MLCL AT1, or ALCAT1 mRNA and cardiolipin content and composition in a biological sample from the subject for monitoring of treatment for heart failure.

Methods

For cardiolipin measurements, lipids are extracted from cellular samples from the subject, such as including, but not limited to, cardiac tissue, non-cardiac tissue, peripheral blood cells, such as peripheral blood mononuclear cells (PBMCs) and leukocytes, and isolated mitochondria. Lipids are extracted from the sample with a chloroform/methanol solution (Bligh Dyer extraction). Individual lipid extracts are reconstituted with chloroform:methanol (1:1), flushed with $N_2$, and stored at −20° C. for analysis via electrospray ionization mass spectroscopy using a triple-quadrupole mass spectrometer equipped with an automated nanospray apparatus. Enhanced multidimensional mass spectrometry-based shotgun lipidomics for cardiolipin is performed as described by Han, et al., "*Shotgun lipidomics of cardiolipin molecular species in lipid extracts of biological samples,*" *J Lipid Res* 47(4)864-879 (2006). Illustrative results for this analysis are shown in Example 1 above.

For mRNA measurements, RNA is prepared from cellular samples from the subject, such as including, but not limited to, cardiac tissue, non-cardiac tissue, peripheral blood cells, such as peripheral blood mononuclear cells (PBMCs) and leukocytes, and isolated mitochondria. Levels of mRNAs are measured using methods known in the art, such as those exemplified in Example 2 above.

Results

It is expected that individuals with heart failure will display aberrant levels of one or more of TAZ1, MLCL AT1, and ALCAT1 mRNAs compared to a normal control subject. TAZ1 mRNAs are expected to be reduced compared to the control, while MLCL AT1, and ALCAT1 mRNAs are expected to be elevated. It is further expected that subjects with heart failure will display aberrant cardiolipin remodeling compared to a normal control subject, with reduced levels of the 18:2 cardiolipin species compared to a control. Accordingly, these measurements are an indicator of the relative success of treatment for heart failure in a given individual.

Results for a given individual may be compared to results for a normal control subject, or to previous results obtained for the subject, in order to assess relative improvement of the subject over the course of time. Where a subject shows satisfactory or unsatisfactory levels of TAZ1, MLCL AT1, and ALCAT1 mRNAs or cardiolipin content or composition, the heart failure treatment may be adjusted accordingly.

These results will show that the methods of the present technology are useful for detecting the levels of TAZ1, MLCL AT1, and ALCAT1 mRNAs mRNA and cardiolipin content and composition for monitoring heart failure treatment in a subject in need thereof.

Example 5: Assessing Mitochondrial Dysfunction

This example will demonstrate methods of the present technology for assessing mitochondrial dysfunction in a subject in need thereof. In particular, the example will demonstrate the detection of TAZ1, MLCL AT1, or ALCAT1 mRNA and cardiolipin content and composition in a biological sample from the subject for assessing mitochondrial dysfunction.

Methods

For cardiolipin measurements, lipids are extracted from cellular samples from the subject, such as including, but not limited to, cardiac tissue, non-cardiac tissue, peripheral blood cells, such as peripheral blood mononuclear cells (PBMCs) and leukocytes, and isolated mitochondria. Lipids are extracted from the sample with a chloroform/methanol solution (Bligh Dyer extraction). Individual lipid extracts are reconstituted with chloroform:methanol (1:1), flushed with $N_2$, and stored at −20° C. for analysis via electrospray ionization mass spectroscopy using a triple-quadrupole mass spectrometer equipped with an automated nanospray apparatus. Enhanced multidimensional mass spectrometry-based shotgun lipidomics for cardiolipin is performed as described by Han, et al., "*Shotgun lipidomics of cardiolipin molecular species in lipid extracts of biological samples,*" *J Lipid Res* 47(4)864-879 (2006). Illustrative results for this analysis are shown in Example 1 above.

For mRNA measurements, RNA is prepared from cellular samples from the subject, such as including, but not limited to, cardiac tissue, non-cardiac tissue, peripheral blood cells, such as peripheral blood mononuclear cells (PBMCs) and leukocytes, and isolated mitochondria. Levels of mRNAs are measured using methods known in the art, such as those exemplified in Example 2 above.

Results

It is expected that individuals with mitochondrial dysfunction will display aberrant levels of one or more of TAZ1, MLCL AT1, and ALCAT1 mRNAs compared to a normal control subject. TAZ1 mRNAs are expected to be reduced compared to the control, while MLCL AT1, and ALCAT1 mRNAs are expected to be elevated. It is further expected that subjects with heart failure will display aberrant cardiolipin remodeling compared to a normal control subject, with reduced levels of the 18:2 cardiolipin species compared to a control.

These results will show that the methods of the present technology are useful for detecting the levels of TAZ1, MLCL AT1, and ALCAT1 mRNA and cardiolipin content and composition for assessing mitochondrial dysfunction in a subject in need thereof.

Example 6: Assessing Mitochondrial Cardiolipin Content and Composition

This example will demonstrate methods of the present technology for assessing mitochondrial cardiolipin content and composition in a subject in need thereof.

Methods

Lipids are extracted from cellular samples from the subject, such as including, but not limited to, cardiac tissue, non-cardiac tissue, peripheral blood cells, such as peripheral blood mononuclear cells (PBMCs) and leukocytes, and isolated mitochondria. Lipids are extracted from the sample with a chloroform/methanol solution (Bligh Dyer extraction). Individual lipid extracts are reconstituted with chloroform:methanol (1:1), flushed with $N_2$, and stored at −20° C. for analysis via electrospray ionization mass spectroscopy using a triple-quadrupole mass spectrometer equipped with an automated nanospray apparatus. Enhanced multidimensional mass spectrometry-based shotgun lipidomics for cardiolipin is performed as described by Han, et al., "*Shot-* gun lipidomics of cardiolipin molecular species in lipid extracts of biological samples," *J Lipid Res* 47(4)864-879 (2006). Illustrative results for this analysis are shown in Example 1 above.

Results

It is expected that individuals with mitochondrial dysfunction or heart failure will display aberrant levels of one or more of TAZ1, MLCL AT1, and ALCAT1 mRNAs compared to a normal control subject. TAZ1 mRNAs are expected to be reduced compared to the control, while MLCL AT1, and ALCAT1 mRNAs are expected to be elevated. It is further expected that subjects with heart failure will display aberrant cardiolipin remodeling compared to a normal control subject, with reduced levels of the 18:2 cardiolipin species compared to a control.

These results will show that the methods of the present technology are useful for assessing cardiolipin content and composition in a subject in need thereof. The assessment may be made, for example, in the context of diagnosing heart failure, monitoring the treatment of heart failure, or assessing mitochondrial dysfunction, such as described in the above examples.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A method for monitoring and treating a subject for heart failure, the method comprising:
   (a) detecting levels of monolysocardiolipin acyltransferase (MLCL AT1) or acyl-CoA lysocardiolipin (ALCAT1) mRNA in a biological sample from the subject;
   (b) selecting the subject for aromatic-cationic peptide treatment where the level of MLCL AT1 or ALCAT1 mRNA in the biological sample from the subject is elevated about 2.5-fold compared to a normal control sample; and
   (c) administering to the subject a therapeutically effective amount of the aromatic-cationic peptide, wherein the aromatic-cationic peptide is D-Arg-2'6'-Dmt-Lys-Phe-NH$_2$ or a pharmaceutically acceptable salt thereof, wherein treatment increases the expression of TAZ1 in the myocardium of the subject.

2. The method of claim 1, further comprising detecting levels of cardiolipin isoforms in a biological sample from the subject and comparing the levels of cardiolipin isoforms to those of a normal control subject, wherein the detecting levels of cardiolipin isoforms comprises chromatography, mass spectrometry, ELISA, Western blotting, immunodetection, or immunoprecipitation.

3. The method of claim 1, wherein detecting the level of MLCL AT1 or ALCAT1 mRNA comprises RT-PCR, in situ hybridization, or Northern blotting.

4. The method of claim 1, wherein the peptide is administered daily for 6 weeks or more.

5. The method of claim 1, wherein the heart failure results from hypertension; ischemic heart disease; exposure to a cardiotoxic compound; myocarditis; thyroid disease; viral infection; gingivitis; drug abuse; alcohol abuse; pericarditis; atherosclerosis; vascular disease; hypertrophic cardiomyopathy; acute myocardial infarction; left ventricular systolic dysfunction; coronary bypass surgery; starvation; an eating disorder; or a genetic defect.

6. The method of claim 1, wherein the peptide is administered orally, topically, systemically, intravenously, subcutaneously, intraperitoneally, or intramuscularly.

7. The method of claim 1, further comprising separately, sequentially or simultaneously administering a cardiovascular agent to the subject, wherein the cardiovascular agent is selected from the group consisting of: an anti-arrhythmia agent, a vasodilator, an anti-anginal agent, a corticosteroid, a cardioglycoside, a diuretic, a sedative, an angiotensin converting enzyme (ACE) inhibitor, an angiotensin II antagonist, a thrombolytic agent, a calcium channel blocker, a throboxane receptor antagonist, a radical scavenger, an anti-platelet drug, a β-adrenaline receptor blocking drug, α-receptor blocking drug, a sympathetic nerve inhibitor, a *digitalis* formulation, an inotrope, and an antihyperlipidemic drug.

8. The method of claim 1, wherein the biological sample comprises tissue, a cell, or a mitochondrion from the subject.

* * * * *